(12) United States Patent
Cook, Jr.

(10) Patent No.: US 10,242,154 B1
(45) Date of Patent: Mar. 26, 2019

(54) **CLINICAL USE OF AN *ALU* ELEMENT BASED BIOINFORMATICS METHODOLOGY FOR THE DETECTION AND TREATMENT OF CANCER**

(71) Applicant: George Wyndham Cook, Jr., Baton Rouge, LA (US)

(72) Inventor: George Wyndham Cook, Jr., Baton Rouge, LA (US)

( * ) Notice: Subject to any disclaimer, the term of this patent is extended or adjusted under 35 U.S.C. 154(b) by 115 days.

(21) Appl. No.: 14/832,277

(22) Filed: Aug. 21, 2015

Related U.S. Application Data

(63) Continuation-in-part of application No. 14/154,303, filed on Jan. 14, 2014, now abandoned.

(60) Provisional application No. 62/040,481, filed on Aug. 22, 2014.

(51) Int. Cl.
*G06F 19/00* (2018.01)
*G06F 19/24* (2011.01)
*C12Q 1/6886* (2018.01)

(52) U.S. Cl.
CPC ........... *G06F 19/24* (2013.01); *C12Q 1/6886* (2013.01)

(58) Field of Classification Search
CPC .......... G06F 19/18; G06F 19/22; G06F 19/20; G06F 19/24; G06F 19/3431; G06F 19/345; G06F 19/12; G06F 19/16; G06F 19/3487; G01N 33/574
See application file for complete search history.

(56) References Cited

PUBLICATIONS

Lee, E. et al. Landscape of Somatic Retrotransposon in Human Cancers. Science 2012 vol. 334 pp. 967-971.*
Jane E. Visvader, Cells of origin in cancer, Nature, Jan. 20, 2011, 314-322, 469.
Lucy Yates & Peter Campbell, Evolution of the Cancer Genome, Nature Reviews Genetics, Nov. 2012, 795-806, 13-11.
Levi Garraway & Eric Lander, Lessons from the Cancer Genome, Cell, Mar. 28, 2013, 17-37, 153.
Christopher Greenman, Philip Stephens, et al., Patterns of somatic mutation in human cancer genomes, Nature Mar. 8, 2007: 153-158, 446.

(Continued)

*Primary Examiner* — Mary K Zeman

(57) ABSTRACT

The present invention describes a bioinformatic method that can be used in the estimation of an individual's susceptibility to cancer through an evaluation of that individual's personal genome sequence. More specifically, this invention is a continuation-in-part of the methodology described in patent application Ser. No. 14/154,303 for the early detection of cancer. Said method is based upon an analysis of the structure of the repetitive DNA sequences surrounding and within the various cancer-linked regions of the individual's genome being evaluated. Said analysis of said individual's genome is then compared to the same analysis conducted for one or more reference genomes and/or genes for which cancer susceptibility has been previously determined. Said analysis can also be used to estimate the respective likelihoods that each cancer-linked genomic region will be damaged in the potential formation of a tumor. This patient-specific analysis can then be used in the economical design of locus-specific monitoring for early genetic damage as part of pre-cancer genetic screening.

1 Claim, 22 Drawing Sheets

(56) References Cited

PUBLICATIONS

Laura E. MacConaill & Levi Garraway, Clinical Implications of the Cancer Genome, Journal of Clinical Oncology, 2010 Dec. 10, 2010, 5219-5228,28-35.

Simon Forbes, Nidhi Bindal et al., COSMIC: mining complete cancer genomes in the Catalogue of Somatic Mutations in Cancer, Nucleic Acids Research, Jan. 2011, vol. 39, D945-D950, 39.

George Cook, Miriam Konkel, et al. Alu pair exclusions in the human genome, Mobile DNA, Sep. 23, 2011, 1-16, 2-10.

Prescott Deininger & Mark Batzer, Alu Repeats and Human Disease, Molecular Genetics and Metabolism, 1999, 183-193, 67.

Dale Hedges & Prescott Deininger, Inviting Instability: Transposable elements, Double-strand breaks, and the Maintenance of Genome Integrity, Mutation Research, Mar. 1, 2007, 46-59, 616-1 &2.

Miriam Konkel and Mark Batzer, A mobile threat to genome stability: The impact of non-LTR retrotransposons upon the human genome, Seminars in Cancer Biology, 2010, 211-221.

George Cook, Miriam Konkel, et al., A Comparison 100 Human Genes Using an Alu Element-Based Instability Model, PLOS ONE, Jun. 2013 3,1-14, 8-6.

Jerzy Jurka, Oleksiy Kohany, et al., Duplication, coclustering, and selection of human Alu retrotransposons, Proceeding of the National Academy of Sciences, Feb. 3, 2004, 1268-1272, 101-5.

Adam De Smith, Robin Walters, et al., Small Deletion Variants Have Stable Breakpoints Commonly Associated with Alu Elements, PLOS ONE, Aug. 2008, 1-11, 3-8.

Jungnam Lee, Kyudong Han, et al., Chromosomal Inversions between Human and Chimpanzee Lineages Caused by Retrotransposons, PLOS ONE, Dec. 2008, 1-9, 3-12.

James Lupski, Retrotransposition and Structural Variation in the Human Genome, Cell, Jun. 25, 2010, 1110-1112, 141.

Shurjo Sen, Kyudong Han, et al., Human Genomic Deletions Mediated by Recombination between Alu Elements, The American Journal of Human Genetics, Jul. 2006, 41-53, 79.

Kirill Lobachev, Judith Stenger, et al., Inverted Alu repeats unstable in yeast are excluded from the human genome, EMBO Journal, 2000, 19-14.

Judith Stenger, Kirill Lobachev, et al., Biased Distribution of Inverted and Direct Alus in the Human Genome: Implications for Insertion, Exclusion, and Genome Stability, Genome Research, 2001, 12-27, 11.

Kunio Kitada, Satoko Aikawa, et al., Alu-Alu Fusion Sequences Identified at Junction Sites of Copy Number Amplified Regions in Cancer Cell Lines, Cytogenetic and Genomic Reseach, Jan. 1-8, 2013, 139.

Jeffrey Kidd, Tina Graves, et al., A Human Genome Structural Variation Sequencing Resource Reveals Insights into Mutational Mechanisms, Cell, Nov. 24, 2010, 837-847, 143.

David Cooper, Albino Bacolla, et al., On the Sequence-Directed Nature of Human Gene Mutation: The Role of Genomic Architecture and the Local DNA Environment in Mediating Gene Mutations Underlying Human Inherited Disease, Human Mutation, 2011, 1075-1099, 32-10.

Ivy Jennes, Danielle Jong, et al., Breakpoint characterization of large deletions in EXT1 or EXT2 in 10 Multiple Osteochondromas families, BMC Medical Genetics, 2011, 1-9, 12-85.

Jan Korbel, Alexander Urban, et al., Paired-End Mapping Reveals Extensive Structural Variation in the Human Genome, Science, Oct. 19, 2007, 420-426, 318.

Kyudong Han, Jungnam Lee, et al., L1 recombination-associated deletions generate human genomic variation, Proceedings of the National Academy of Sciences, Dec. 9, 2008, 19365-19370, 105-49.

Carlos Prada & Paul Laissue, A high resolution map of mammalian X chromosome fragile regions assessed by large-scale comparative genomics, 2014, 618-635, 25.

Richard Boland, Stephan Thibodeau, et al., A National Cancer Institute Workshop on MicrosatelliteInstability for Cancer Detection and Familial Predispositiona: Development of International Criteria for the Determination of Microsatellite Instability in Colorectal Cancer, Cancer Research, Nov. 5, 1998, 5248-5257, 58.

Homaira Nawroz-Danish, Claus Eisenberger, et al. Microsatellite Analysis of the Serum DNA in Patients with Head and Neck Cancer, International Journal of Cancer, 2004, 96-100, 111.

Guruprasad Ananda, Suzanne Hile, et al., Microsatellite Interruptions Stabilize Primate Genomes and Exist as Population-Specific Single Nucleotide Polymorphisms within Individual Human Genomes, PLOS ONE, Jul. 17, 2014, 1-19, 10-7.

Jeffrey Weitzel, Shaofeng Ding, et al., The HRAS1 Minisatellite Locus and Risk of Ovarian Cancer, Cancer Research, Jan. 15, 2005, 259-261,60.

Thomas Willems, Melissa Gymrek, et al., The landscape of human STR variation, Genome Research, Aug. 18, 2014, 1894-1904, 24.

Nevim Aygun, Correlations between long inverted repeat (LIR) features, deletion size and distance from breakpoint in human gross gene deletions, Scientific Reports, Feb. 6, 2015, 1-12, 5-8300.

Kunio Kitada, Tomoaki Yamasaki, et al., The MDR1/ABCB1 regional amplification in large inverted repeats with asymmetric sequences and microhomologies at the junction sites, Cancer Genetics and Cytogenetic, 2007, 120-127, 178.

Philip Boone, Pengfei Liu, et al., Alu-specific microhomology-mediated deletion of the final exon of SPAST in three unrelated subjects with hereditary spastic paraplegia, Genetics in Medicine, Jun. 2011, 582-592, 13-6.

Hannah Verdin, Barbara D'Haene, et al., Microhomology-Mediated Mechanisms Underlie Non-Recurrent Disease-Causing Microdeletions of the FOXL2Gene or Its Regulatory Domain, PLOS, Mar. 4, 2013, 1-12, 9-3.

Diego Ottaviani, Magdalena Lecain, et al., The role of microhomology in genomic structural variation, Trends in Genetics, Mar. 2014, 95-94, 30-3.

David Wheeler, Maithreyan Srinivasan, et al., The complete genome of an individual by massively parallel DNA sequencing, Nature, Apr. 17, 2008, 872-877,452.

Genomes Project (Goncalo Abecasis, Adam Auton, et al.), et al., An integrated map of genetic variation from 1,092 human genomes, Nature, Nov. 1, 2012, 56-65, 491.

Lynn Jorde & Stephen Wooding, Genetic variation, classification and 'race', Nature Genetics, S28-S32,36-11.

Ryan Mills, Stephen Pittard, et al., Natural genetic variation caused by small insertions and deletions in the human genome, Genome Research, Apr. 1, 2011, 830-839, 21.

Richard Redon, Shumpei Ishikaww, et al., Global variation in copy number in the human genome, Nature, Nov. 23, 2006, 444-455, 444.

Mark Chaisson, John Huddleston, et al., Resolving the complexity of the human genome using single-molecule sequencing, Nature, Jan. 29, 2015, 608-618, 517.

Carl Bruder, Arkadiusz Piotrowski, et al., Phenotypically Concordant and Discordant Monozygotic Twins Display Different DNA Copy-Number-Variation Profiles, The American Journal of Human Genetics, Mar. 2008, 763-771, 82.

Bert Vogelstein, Nickolas Papadopoulos, et al., Cancer Genome Landscapes, Science, Mar. 29, 2013, 1546-1558, 339.

Michael McConnell, Michael Lindberg, et al., Mosaic Copy Number Variation in Human Neurons, Science, Nov. 1, 2013, 632-637, 342.

Rebecca Burrell, Nicholas McGranahan, et al., The causes and consequences of genetic heterogeneity in cancer evolution, Nature, Sep. 19, 2013, 338-345, 501.

Maryam Heidary, Marina Auer, et al., The dynamic range of circulating tumor DNA in metastatic breast cancer, Breast Cancer Research, Aug. 9, 2014, 1-10,16-421.

Jens Lorh, Petar Stojanov, et al., Widespread genetic heterogeneity in multiple myeloma: implications for targeted therapy, Cancer Cell, Jan. 13, 2014, 91-101, 25-1.

Christopher Ricketts, Marston Linehan, et al., Intratumoral heterogeneity in kidney cancer, Nature Genetics, Mar. 2014, 214-5, 46.

Jianjun Zhang, Junya Fujimoto, et al., Intratumor heterogeneity in localized lung adenocarcinomas delineated by multiregion sequencing, Science, Oct. 10, 2014, 256-9, 346.

Kimberly Allison & George Sledge Jr, Heterogeneity and Cancer, CancerNetwork (home of the journal Oncology), Sep. 15, 2014, 1-9.

(56) References Cited

PUBLICATIONS

David Kass, Mark Batzer, et al., Gene Conversion as a Secondary Mechanism of Short Interspersed Element (SINE) Evolution, Molecular and Cellular Biology, Jan. 1995, 19-25, 15-1.

Astrid Roy, Marion Carroll, et al., Potential Gene Conversion and Source Genes for Recently Integrated Alu Elements, Genome Research, Oct. 2000, 1485-1495, 10.

Degui Zhi, Sequence correlation between neighboring Alu instances suggests post-retrotransposition sequence exchange due to Alu gene conversion, Gene, Apr. 1, 2007, 117-121, 390-1-2.

Alexy Aleshin & Degui Zhi, Recombination-Associated Sequence Homogenization of Neighboring Alu Elements: Signature of Nonallelic Gene Conversion, Journal of Molecular Biology and Evolution, Oct. 2010, 2300-2311, 27-10.

Hans Fogedby & Ralf Metzler, Dynamics of DNA breathing: Weak noise analysis, finite time singularity, and mapping onto the quantum Coulomb problem, Physical Review E, Dec. 21, 2007, 1-12, 061915.

Prabhat Mandal & Haig Kazazian, Snapshot: Verterbrate Transposons, Cell, Oct. 3, 2008, 192-193, 135.

\* cited by examiner

Figure 1

**Selected Studies Reporting Disease Related *Alu* Element Mediated Deletions**[1]

| First Author | Journal | Year of Publication | Deletion No. | Deletion Size, bp | Disease Gene |
|---|---|---|---|---|---|
| Vaughn, CP | GC&C[2] | 2013 | 1 | ~1,500 | *PMS2* |
| | | | 2 | ~2,000 | *PMS2* |
| | | | 3 | ~2,000 | *PMS2* |
| Duraturo, F | BRI[3] | 2013 | 1 | 9,655 | *MSH2* |
| Pezzoli, L | Gene | 2012 | 1 | 3,505 | *MYBPC3* |
| Pereria, MC | GiM[4] | 2012 | 1 | 1,056 | *SPG11* |
| | | | 2 | 1,489 | *SPG11* |
| | | | 3 | 8,323 | *SPG11* |
| | | | 4 | 2,710 | *SPG11* |
| Mahmoudi, H | ED[5] | 2012 | 1 | 12,200 | *LPAR6* |
| Jelassi, A | CCA[6] | 2012 | 1 | 12,684 | *LDLR* |
| | | | 2 | 2,364 | *LDLR* |
| Silva, AG | BMC Cancer | 2012 | 1 | 36,400 | *BRCA1* |
| Eiden-Plach, A. | JSB&MB[7] | 2012 | 1 | 12,100 | *StAR* |
| Coutinho, MF | JIMD[8] | 2012 | 1 | 897 | *GNPTAB* |
| Chanavat, V | EJMG[9] | 2012 | 1 | 3,505 | *MYBPC3* |
| Bondurand, D | EJMG | 2012 | 1 | 56,600 | *SOX10* |
| Barbaro, M | IJGM&PM[10] | 2012 | 1 | 3,381 | *CPOX* |

(1) Citations from {11}(Cook et al. 2013)
(2) *Genes, Chromosomes & Cancer*
(3) *Biomed Research International*
(4) *Genetics in Medicine*
(5) *Experimental Dermatology*
(6) *Clinica Chimica Acta*
(7) *Journal of Steroid Biochemistry & Molecular Biology*
(8) *Journal of Inherited Metabolic Disease*
(9) *European Journal of Medical Genetics*
(10) *International Journal of Genetic, Molecular and Personalized Medicine*

Figure 2
Overview of Selected Human Repetitive Elements

| Repetitive Element | Copies[1] (x $10^{-3}$) | Avg. Length (base pairs) | Percent of Genome[2] | Element Frequency (per $10^6$ base pairs) |
|---|---|---|---|---|
| *Alu* | 1,239 | 260 | 10.56 | 406 |
| MIR | 603 | 143 | 2.83 | 143 |
| SVA | 5.8 | 775 | 0.15 | 1.9 |
| LINE1 (L1) | 961 | 548 | 17.27 | 315 |
| LINE2 (L2) | 474 | 224 | 3.49 | 156 |
| LINE3 (L3) | 56 | 186 | 0.34 | 18 |
| LTR Retrotransposons | 754 | 370 | 9.14 | 247 |
| DNA Transposons | 502 | 210 | 3.46 | 165 |
| Microsatellite VNTR[3] (~2-9 bases)$_n$ | 704 | 55 | 1.27 | 231 |
| Minisatellite VNTR[3] (~10-60 bases)$_n$ | 4.6 | 915 | 0.14 | 1.5 |
| Low Complexity | 103 | 61 | 0.21 | 34 |
| Total | | | 48.84 % | 1,773 |

(1) Taken from hg38 (December 2013) human genome assembly from UCSC Table Browser
(2) Taken from {56}-(Mandal and Kazazian 2008)
(3) VNTR, Variable Number of Tandem Repeats

Figure 4

| | Inverted:Direct (I:D) Pair Orientation Ratios for Selected Repetitive Element Pairs in the Human Genome, hg38 *(pair sequence numbers (PSNs) 11-30, 95% confidence intervals shown below each I:D value)* | | | | | | | |
|---|---|---|---|---|---|---|---|---|
| Human Repetitive DNA Elements → (approx. percent of total hg38 sequence) ↓ | *Alu* (10.56%) | MIR (2.83%) | SVA (0.15%) | LINE1 (L1) (17.27%) | LINE2 (L2) (3.49%) | LINE3 (L3) (0.34%) | LTR Retro-Transposons (9.14%) | DNA Transposons (2.34%) |
| SINEs — *Alu* | 0.971 (± 0.0008) | | | | | | | |
| SINEs — MIR | 1.002 (± 0.0008) | 0.999 (± 0.0017) | | | | | | |
| SINEs — SVA | 0.917 (± 0.0089) | 1.001 (± 0.0103) | 0.942 (± 0.0183) | | | | | |
| LINEs — LINE1 (L1) | 0.946 (± 0.0007) | 1.006 (± 0.0010) | 0.878 (± 0.0100) | 0.931 (± 0.0008) | | | | |
| LINEs — LINE2 (L2) | 0.994 (± 0.0008) | 1.002 (± 0.0019) | 0.993 (± 0.0132) | 0.986 (± 0.0012) | 0.996 (± 0.0009) | | | |
| LINEs — LINE3 (L3) | 1.000 (± 0.0023) | 0.998 (± 0.0023) | 0.986 (± 0.0105) | 1.002 (± 0.0027) | 1.001 (± 0.0026) | 0.999 (± 0.0044) | | |
| LTR Retro-transposons | 0.983 (± 0.0007) | 1.002 (± 0.0012) | 0.950 (± 0.0118) | 0.950 (± 0.0009) | 0.985 (± 0.0013) | 0.996 (± 0.0020) | 0.968 (± 0.0007) | |
| DNA Transposons | 0.996 (± 0.0011) | 1.001 (± 0.0012) | 0.997 (± 0.0098) | 0.992 (± 0.0012) | 0.999 (± 0.0018) | 0.997 (± 0.0019) | 0.995 (± 0.0013) | 1.000 (± 0.0009) |

Shaded Blocks Indicate a Statistical Departure from Unity (p<0.05) and Suggest Possible Pair Interaction (Underlined Values, less than 0.98)

Figure 5

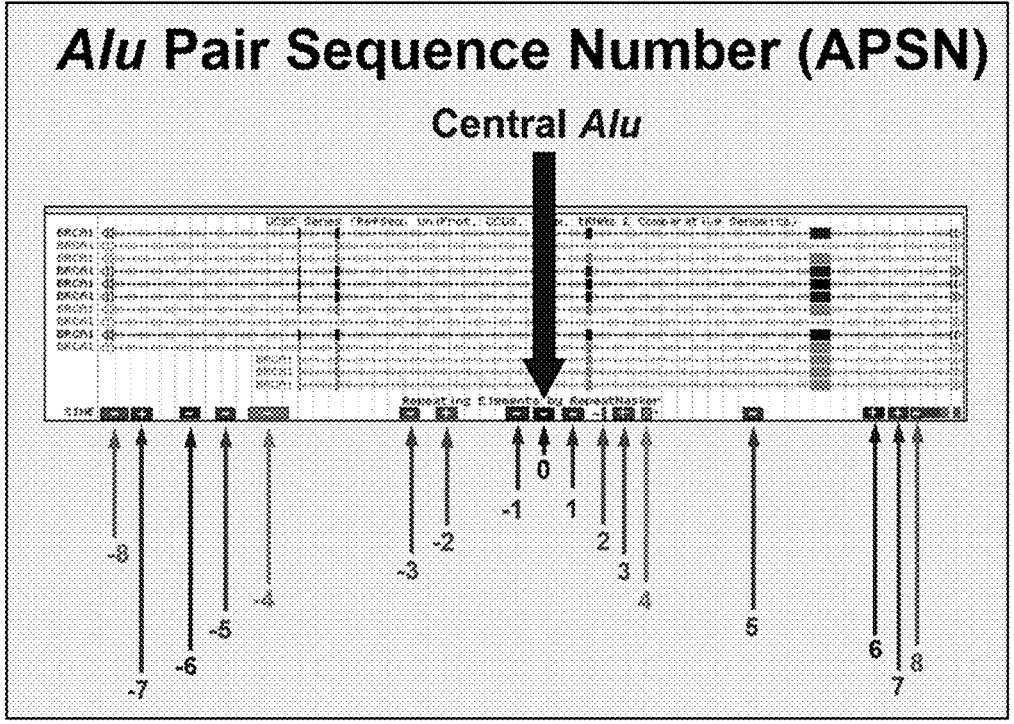

*Alu* Pair Sequence Number (APSN)

Central *Alu*

Figure 21

*BRCA1* Repetitive DNA Landscape
(Human genome assembly, hg38)

| Chromosome ID | Sequence Start | Sequence End | Length (bp) | Repeat Orientation or Exon Direction | Repeat or Gene ID | Repeat Subfamily[1] or Exon Number |
|---|---|---|---|---|---|---|
| chr17 | 43,044,294 | 43,045,802 | 1,507 | ↑ | *BRCA1* | Exon 23 |
| chr17 | 43,044,793 | 43,045,101 | 309 | - | Alu | AluSx1 |
| chr17 | 43,045,922 | 43,046,222 | 301 | - | Alu | AluSx |
| chr17 | 43,046,222 | 43,046,397 | 176 | - | Alu | AluSq2 |
| chr17 | 43,046,397 | 43,046,648 | 252 | - | Alu | AluSx |
| chr17 | 43,046,649 | 43,046,773 | 125 | + | Alu | AluSx3 |
| chr17 | 43,046,917 | 43,047,092 | 176 | + | L1 | L1ME4a |
| chr17 | 43,047,101 | 43,047,400 | 300 | - | Alu | AluJr |
| chr17 | 43,047,642 | 43,047,703 | 60 | ↑ | *BRCA1* | Exon 22 |
| chr17 | 43,047,743 | 43,047,771 | 29 | - | Alu | AluJo |
| chr17 | 43,047,771 | 43,048,051 | 281 | - | Alu | AluJb |
| chr17 | 43,048,051 | 43,048,192 | 142 | - | Alu | AluJo |
| chr17 | 43,048,197 | 43,048,503 | 307 | - | Alu | AluSc |
| chr17 | 43,048,503 | 43,048,817 | 315 | - | Alu | AluSz |
| chr17 | 43,049,120 | 43,049,194 | 73 | ↑ | *BRCA1* | Exon 21 |
| chr17 | 43,049,536 | 43,049,562 | 27 | + | Simple Repeat | (CCTT)n |
| chr17 | 43,050,326 | 43,050,633 | 308 | + | Alu | AluSc8 |
| chr17 | 43,051,062 | 43,051,117 | 54 | ↑ | *BRCA1* | Exon 20 |
| chr17 | 43,051,638 | 43,051,934 | 297 | - | Alu | AluSg |
| chr17 | 43,052,140 | 43,052,278 | 139 | + | DTr | hAT-Charlie |
| chr17 | 43,052,278 | 43,052,444 | 167 | - | Alu | AluJo |
| chr17 | 43,052,444 | 43,052,508 | 65 | + | DTr | hAT-Charlie |
| chr17 | 43,052,780 | 43,052,824 | 45 | + | Simple Repeat | (AC)n |
| chr17 | 43,052,878 | 43,053,139 | 262 | - | Alu | AluSx3 |

(1) The sequence of Simple Repeats and Low Complexity repeats sequences are described in Column 7 and Exons are double-underlined in bold.

Figure 21, continued

| Chromosome ID | Sequence Start | Sequence End | Length (bp) | Repeat Orientation or Exon Direction | Repeat or Gene ID | Repeat Subfamily[1] or Exon Number |
|---|---|---|---|---|---|---|
| chr17 | 43,053,364 | 43,053,380 | 17 | + | Simple Repeat | (GAAGTTT)n |
| chr17 | 43,053,380 | 43,053,681 | 302 | + | *Alu* | *Alu*Y |
| chr17 | 43,053,681 | 43,053,693 | 13 | + | Simple Repeat | (GAAGTTT)n |
| chr17 | 43,053,693 | 43,053,988 | 296 | + | *Alu* | *Alu*Sp |
| chr17 | 43,053,988 | 43,053,998 | 11 | + | Simple Repeat | (GAAGTTT)n |
| chr17 | 43,054,443 | 43,054,739 | 297 | - | *Alu* | *Alu*Jb |
| chr17 | 43,054,744 | 43,055,049 | 306 | - | *Alu* | *Alu*Sq2 |
| chr17 | 43,055,199 | 43,055,265 | 67 | + | MIR | MIRc |
| chr17 | 43,055,333 | 43,055,365 | 33 | + | MIR | MIR |
| chr17 | 43,055,365 | 43,055,502 | 138 | + | *Alu* | *Alu*Sz6 |
| chr17 | 43,055,502 | 43,055,777 | 276 | + | *Alu* | *Alu*Sx |
| chr17 | 43,055,777 | 43,055,960 | 184 | + | *Alu* | *Alu*Sz6 |
| chr17 | 43,055,960 | 43,056,172 | 213 | + | MIR | MIR |
| chr17 | 43,056,172 | 43,056,478 | 307 | - | *Alu* | *Alu*Jb |
| chr17 | 43,056,478 | 43,056,510 | 33 | + | MIR | MIR |
| chr17 | 43,056,511 | 43,056,692 | 182 | + | *Alu* | *Alu*Sx |
| chr17 | 43,056,713 | 43,056,970 | 258 | + | MIR | MIRb |
| chr17 | 43,057,051 | 43,057,135 | 83 | ↑ | *BRCA1* | Exon 19 |
| chr17 | 43,057,227 | 43,057,550 | 324 | + | *Alu* | *Alu*Sx1 |
| chr17 | 43,057,553 | 43,057,863 | 311 | + | *Alu* | *Alu*Y |
| chr17 | 43,057,864 | 43,058,045 | 182 | + | *Alu* | *Alu*Sz6 |
| chr17 | 43,058,078 | 43,058,380 | 303 | + | *Alu* | *Alu*Jr |
| chr17 | 43,058,380 | 43,058,429 | 50 | + | Simple Repeat | (CA)n |
| chr17 | 43,059,096 | 43,059,181 | 86 | + | L2 | L2a |
| chr17 | 43,059,181 | 43,059,469 | 289 | + | *Alu* | *Alu*Sx1 |
| chr17 | 43,059,469 | 43,059,515 | 47 | + | Simple Repeat | (ACA)n |
| chr17 | 43,059,515 | 43,059,762 | 248 | + | L2 | L2a |

(1) The sequence of Simple Repeats and Low Complexity repeats sequences are described in Column 7 and Exons are double-underlined in bold.

Figure 21, continued

| Chromosome ID | Sequence Start | Sequence End | Length (bp) | Repeat Orientation or Exon Direction | Repeat or Gene ID | Repeat Subfamily[1] or Exon Number |
|---|---|---|---|---|---|---|
| chr17 | 43,059,898 | 43,059,918 | 21 | + | Simple Repeat | (TAT)n |
| chr17 | 43,059,918 | 43,060,072 | 155 | - | Alu | AluSx |
| chr17 | 43,060,072 | 43,060,341 | 270 | - | Alu | AluSp |
| chr17 | 43,060,341 | 43,060,484 | 144 | - | Alu | AluSx |
| chr17 | 43,060,484 | 43,060,502 | 19 | + | Simple Repeat | (TAT)n |
| chr17 | 43,060,502 | 43,060,806 | 305 | - | Alu | AluSz |
| chr17 | 43,060,843 | 43,061,154 | 312 | + | Alu | AluSz |
| chr17 | 43,061,169 | 43,061,510 | 342 | + | L2 | L2a |
| chr17 | 43,061,585 | 43,061,884 | 300 | - | Alu | AluSz |
| chr17 | 43,062,098 | 43,062,392 | 295 | - | Alu | AluJr4 |
| chr17 | 43,062,602 | 43,062,893 | 292 | - | Alu | AluSx |
| chr17 | 43,062,894 | 43,063,183 | 290 | - | Alu | AluSp |
| chr17 | 43,063,332 | 43,063,373 | 40 | ↑ | *BRCA1* | Exon 18 |
| chr17 | 43,063,873 | 43,063,951 | 77 | ↑ | *BRCA1* | Exon 17 |
| chr17 | 43,064,623 | 43,064,660 | 38 | + | Simple Repeat | (CAG)n |
| chr17 | 43,064,827 | 43,065,128 | 302 | - | Alu | AluYm1 |
| chr17 | 43,065,386 | 43,065,694 | 309 | + | Alu | AluSp |
| chr17 | 43,065,734 | 43,066,213 | 480 | - | L3 | L3 |
| chr17 | 43,066,409 | 43,066,707 | 299 | - | Alu | AluSx4 |
| chr17 | 43,066,812 | 43,067,117 | 306 | - | Alu | AluSq2 |
| chr17 | 43,067,239 | 43,067,553 | 315 | - | Alu | AluSc |
| chr17 | 43,067,607 | 43,067,695 | 87 | ↑ | *BRCA1* | Exon 16 |
| chr17 | 43,067,763 | 43,067,836 | 74 | + | L1 | L1PA8 |
| chr17 | 43,067,836 | 43,067,888 | 53 | - | Alu | AluSz6 |
| chr17 | 43,067,890 | 43,067,912 | 23 | + | Simple Repeat | (A)n |
| chr17 | 43,067,995 | 43,068,290 | 296 | + | Alu | AluY |
| chr17 | 43,068,344 | 43,068,417 | 74 | + | Low Complexity | A-rich |

(1) The sequence of Simple Repeats and Low Complexity repeats sequences are described in Column 7 and Exons are double-underlined in bold.

Figure 21, continued

| Chromosome ID | Sequence Start | Sequence End | Length (bp) | Repeat Orientation or Exon Direction | Repeat or Gene ID | Repeat Subfamily[1] or Exon Number |
|---|---|---|---|---|---|---|
| _chr17_ | _43,070,927_ | _43,071,238_ | _310_ | _↑_ | _BRCA1_ | _Exon 15_ |
| chr17 | 43,068,428 | 43,068,567 | 140 | + | Alu | FLAM_C |
| chr17 | 43,069,933 | 43,070,232 | 300 | - | Alu | AluSp |
| chr17 | 43,071,341 | 43,071,613 | 273 | + | L1 | L1ME4b |
| chr17 | 43,071,721 | 43,072,011 | 291 | + | Alu | AluY |
| chr17 | 43,072,011 | 43,072,044 | 34 | + | Simple Repeat | (AAAT)n |
| chr17 | 43,072,105 | 43,072,395 | 291 | + | Alu | AluSp |
| chr17 | 43,072,409 | 43,072,567 | 159 | - | Alu | AluJr |
| chr17 | 43,072,567 | 43,072,867 | 301 | - | Alu | AluSp |
| chr17 | 43,072,867 | 43,073,002 | 136 | - | Alu | AluJr |
| chr17 | 43,073,054 | 43,073,166 | 113 | + | Alu | AluJr |
| chr17 | 43,073,071 | 43,073,180 | 110 | - | SVA | SVA_A |
| chr17 | 43,073,737 | 43,073,766 | 30 | + | Simple Repeat | (AT)n |
| chr17 | 43,073,766 | 43,074,056 | 291 | - | Alu | AluSx |
| _chr17_ | _43,074,330_ | _43,074,521_ | _190_ | _↑_ | _BRCA1_ | _Exon 14_ |
| chr17 | 43,074,772 | 43,074,947 | 176 | + | Alu | AluSx1 |
| chr17 | 43,074,949 | 43,075,108 | 160 | + | Low Complexity | A-rich |
| chr17 | 43,075,471 | 43,075,514 | 44 | - | L2 | L2c |
| chr17 | 43,075,564 | 43,075,726 | 163 | - | Alu | AluSx1 |
| chr17 | 43,075,845 | 43,076,093 | 249 | + | Alu | AluJb |
| _chr17_ | _43,076,487_ | _43,076,614_ | _126_ | _↑_ | _BRCA1_ | _Exon 13_ |
| chr17 | 43,077,166 | 43,077,190 | 25 | + | Simple Repeat | (A)n |
| chr17 | 43,077,332 | 43,077,633 | 302 | - | Alu | AluSx1 |
| chr17 | 43,077,721 | 43,078,034 | 314 | - | Alu | AluSp |
| chr17 | 43,078,038 | 43,078,088 | 51 | - | Alu | FLAM_C |
| chr17 | 43,078,088 | 43,078,384 | 297 | - | Alu | AluSx1 |
| chr17 | 43,078,384 | 43,078,471 | 88 | - | Alu | FLAM_C |

(1) The sequence of Simple Repeats and Low Complexity repeats sequences are described in Column 7 and Exons are double-underlined in bold.

Figure 21, continued

| Chromosome ID | Sequence Start | Sequence End | Length (bp) | Repeat Orientation or Exon Direction | Repeat or Gene ID | Repeat Subfamily[1] or Exon Number |
|---|---|---|---|---|---|---|
| chr17 | 43,079,174 | 43,079,207 | 34 | + | Simple Repeat | (AAACA)n |
| chr17 | 43,080,191 | 43,080,250 | 60 | - | L2 | L2b |
| chr17 | 43,080,315 | 43,080,495 | 181 | - | Alu | AluSp |
| chr17 | 43,080,522 | 43,080,804 | 283 | + | Alu | AluJo |
| chr17 | 43,080,818 | 43,080,903 | 86 | + | Alu | AluSx3 |
| chr17 | 43,082,403 | 43,082,575 | 171 | ↑ | *BRCA1* | Exon 12 |
| chr17 | 43,083,158 | 43,083,455 | 298 | - | Alu | AluSz |
| chr17 | 43,083,518 | 43,083,582 | 65 | - | L2 | L2a |
| chr17 | 43,083,857 | 43,084,031 | 175 | - | Alu | AluSx1 |
| chr17 | 43,084,031 | 43,084,329 | 299 | - | Alu | AluY |
| chr17 | 43,084,329 | 43,084,464 | 136 | - | Alu | AluSx1 |
| chr17 | 43,085,257 | 43,085,383 | 127 | + | Alu | AluSx4 |
| chr17 | 43,085,981 | 43,086,106 | 126 | - | L1 | L1ME2z |
| chr17 | 43,086,109 | 43,086,148 | 40 | + | Simple Repeat | (AC)n |
| chr17 | 43,086,248 | 43,086,334 | 87 | + | L2 | L2c |
| chr17 | 43,087,022 | 43,087,377 | 356 | + | L1 | L1ME4a |
| chr17 | 43,087,380 | 43,087,691 | 312 | + | Alu | AluSp |
| chr17 | 43,087,740 | 43,088,050 | 311 | - | Alu | AluJb |
| chr17 | 43,088,149 | 43,088,374 | 226 | - | L1 | L1MB3 |
| chr17 | 43,088,383 | 43,088,442 | 60 | - | LTR | ERV1 |
| chr17 | 43,088,443 | 43,088,607 | 165 | - | L1 | L1MB3 |
| chr17 | 43,089,030 | 43,089,333 | 304 | + | Alu | AluSx1 |
| chr17 | 43,089,545 | 43,089,672 | 128 | - | Alu | AluSq |
| chr17 | 43,089,727 | 43,090,030 | 304 | + | Alu | AluJb |
| chr17 | 43,090,193 | 43,090,275 | 83 | + | MIR | MIRc |
| chr17 | 43,090,372 | 43,090,649 | 278 | - | Alu | AluSx1 |
| chr17 | 43,090,718 | 43,090,758 | 41 | + | Simple Repeat | (GT)n |

(1) The sequence of Simple Repeats and Low Complexity repeats sequences are described in Column 7 and Exons are double-underlined in bold.

Figure 21, continued

| Chromosome ID | Sequence Start | Sequence End | Length (bp) | Repeat Orientation or Exon Direction | Repeat or Gene ID | Repeat Subfamily[1] or Exon Number |
|---|---|---|---|---|---|---|
| chr17 | 43,095,845 | 43,095,922 | 76 | ↑ | *BRCA1* | Exon 11 |
| chr17 | 43,090,901 | 43,090,934 | 34 | + | Simple Repeat | (AC)n |
| chr17 | 43,090,943 | 43,091,032 | 88 | ↑ | *BRCA1* | Exon 10 |
| chr17 | 43,091,434 | 43,094,860 | 3,425 | ↑ | *BRCA1* | Exon 9 |
| chr17 | 43,095,299 | 43,095,611 | 313 | + | *Alu* | *Alu*Jb |
| chr17 | 43,096,095 | 43,096,406 | 312 | + | *Alu* | *Alu*Sz |
| chr17 | 43,096,420 | 43,096,590 | 171 | + | *Alu* | *Alu*Sc5 |
| chr17 | 43,096,890 | 43,096,960 | 71 | + | MIR | MIR3 |
| chr17 | 43,096,976 | 43,097,155 | 180 | + | L1 | L1PREC2 |
| chr17 | 43,097,243 | 43,097,289 | 45 | ↑ | *BRCA1* | Exon 8 |
| chr17 | 43,097,374 | 43,097,425 | 52 | - | L2 | L2b |
| chr17 | 43,097,471 | 43,097,602 | 132 | + | *Alu* | *Alu*Sz |
| chr17 | 43,097,614 | 43,097,846 | 233 | + | MIR | MIR |
| chr17 | 43,098,030 | 43,098,316 | 287 | - | *Alu* | *Alu*Jr |
| chr17 | 43,098,369 | 43,098,665 | 297 | - | *Alu* | *Alu*Sx |
| chr17 | 43,098,689 | 43,098,807 | 119 | - | *Alu* | *Alu*Jo |
| chr17 | 43,098,819 | 43,099,121 | 303 | - | *Alu* | *Alu*Sp |
| chr17 | 43,099,259 | 43,099,570 | 312 | - | *Alu* | *Alu*Sp |
| chr17 | 43,099,774 | 43,099,880 | 105 | ↑ | *BRCA1* | Exon 7 |
| chr17 | 43,100,047 | 43,100,167 | 121 | + | *Alu* | *Alu*Jr |
| chr17 | 43,100,338 | 43,100,511 | 174 | - | *Alu* | *Alu*Sc8 |
| chr17 | 43,100,515 | 43,100,524 | 10 | + | Simple Repeat | (GTGTAT)n |
| chr17 | 43,100,524 | 43,100,545 | 22 | + | Simple Repeat | (TATA)n |
| chr17 | 43,100,545 | 43,100,558 | 14 | + | Simple Repeat | (GTGTAT)n |
| chr17 | 43,100,558 | 43,100,702 | 145 | + | Simple Repeat | (TA)n |
| chr17 | 43,100,738 | 43,101,030 | 293 | - | *Alu* | *Alu*Sx |

(1) The sequence of Simple Repeats and Low Complexity repeats sequences are described in Column 7 and Exons are double-underlined in bold.

Figure 21, continued

| Chromosome ID | Sequence Start | Sequence End | Length (bp) | Repeat Orientation or Exon Direction | Repeat or Gene ID | Repeat Subfamily[1] or Exon Number |
|---|---|---|---|---|---|---|
| chr17 | 43,101,192 | 43,101,493 | 302 | - | *Alu* | *Alu*Sx4 |
| chr17 | 43,101,505 | 43,101,801 | 297 | - | *Alu* | *Alu*Sz |
| chr17 | 43,101,907 | 43,102,070 | 164 | - | *Alu* | *Alu*Jo |
| chr17 | 43,102,070 | 43,102,354 | 285 | - | *Alu* | *Alu*Y |
| chr17 | 43,102,357 | 43,102,654 | 298 | - | *Alu* | *Alu*Sc5 |
| chr17 | 43,102,656 | 43,102,945 | 290 | - | *Alu* | *Alu*Jo |
| chr17 | 43,102,945 | 43,103,069 | 125 | - | *Alu* | *Alu*Jo |
| chr17 | 43,103,184 | 43,103,488 | 305 | + | *Alu* | *Alu*Sx |
| chr17 | 43,103,488 | 43,103,619 | 132 | - | *Alu* | FLAM_C |
| chr17 | 43,103,824 | 43,104,025 | 202 | + | *Alu* | *Alu*Sx |
| chr17 | 43,104,025 | 43,104,077 | 53 | + | *Alu* | *Alu* |
| chr17 | 43,104,078 | 43,104,106 | 29 | + | Simple Repeat | (AAG)n |
| chr17 | 43,104,121 | 43,104,261 | 139 | ↑ | *BRCA1* | Exon 6 |
| chr17 | 43,104,526 | 43,104,701 | 176 | - | DTr | TcMar-Tc2 |
| chr17 | 43,104,867 | 43,104,956 | 88 | ↑ | *BRCA1* | Exon 5 |
| chr17 | 43,105,237 | 43,105,539 | 303 | - | *Alu* | *Alu*Jr |
| chr17 | 43,105,696 | 43,105,830 | 135 | - | L2 | L2a |
| chr17 | 43,105,864 | 43,106,145 | 282 | + | *Alu* | *Alu*Jb |
| chr17 | 43,106,455 | 43,106,533 | 77 | ↑ | *BRCA1* | Exon 4 |
| chr17 | 43,106,675 | 43,106,898 | 224 | - | DTr | hAT-Tip100? |
| chr17 | 43,106,902 | 43,107,062 | 161 | + | L1 | L1M4 |
| chr17 | 43,107,062 | 43,107,362 | 301 | - | *Alu* | *Alu*Yj4 |
| chr17 | 43,107,368 | 43,107,667 | 300 | - | *Alu* | *Alu*Sz6 |
| chr17 | 43,107,667 | 43,107,811 | 145 | + | L1 | L1M4 |
| chr17 | 43,107,852 | 43,107,927 | 76 | - | L2 | L2a |
| chr17 | 43,108,062 | 43,108,349 | 288 | + | *Alu* | *Alu*Sz |
| chr17 | 43,108,428 | 43,108,732 | 305 | + | *Alu* | *Alu*Sz6 |

(1) The sequence of Simple Repeats and Low Complexity repeats sequences are described in Column 7 and Exons are double-underlined in bold.

Figure 21, continued

| Chromosome ID | Sequence Start | Sequence End | Length (bp) | Repeat Orientation or Exon Direction | Repeat or Gene ID | Repeat Subfamily[1] or Exon Number |
|---|---|---|---|---|---|---|
| chr17 | 43,108,732 | 43,109,021 | 290 | + | Alu | AluSp |
| chr17 | 43,109,030 | 43,109,069 | 40 | + | Simple Repeat | (TATC)n |
| chr17 | 43,109,069 | 43,109,296 | 228 | - | Alu | AluJr |
| chr17 | 43,109,798 | 43,109,898 | 101 | + | DTr | TcMar-Tigger |
| chr17 | 43,109,898 | 43,110,193 | 296 | - | Alu | AluY |
| chr17 | 43,110,193 | 43,110,291 | 99 | + | DTr | TcMar-Tigger |
| chr17 | 43,110,304 | 43,110,604 | 301 | + | Alu | AluJb |
| chr17 | 43,110,692 | 43,110,813 | 122 | + | Alu | AluSz |
| chr17 | 43,110,818 | 43,111,116 | 299 | + | Alu | AluSx |
| chr17 | 43,111,116 | 43,111,237 | 122 | + | DTr | TcMar-Tigger |
| chr17 | 43,111,237 | 43,111,538 | 302 | + | Alu | AluSx |
| chr17 | 43,111,540 | 43,111,822 | 283 | + | Alu | AluY |
| chr17 | 43,111,822 | 43,111,860 | 39 | + | Simple Repeat | (AAAC)n |
| chr17 | 43,111,860 | 43,111,871 | 12 | + | Alu | AluY |
| chr17 | 43,111,871 | 43,112,094 | 224 | + | DTr | TcMar-Tigger |
| chr17 | 43,112,094 | 43,112,384 | 291 | - | Alu | AluSx4 |
| chr17 | 43,112,384 | 43,112,436 | 53 | + | DTr | TcMar-Tigger |
| chr17 | 43,112,438 | 43,112,626 | 189 | + | Alu | AluJr4 |
| chr17 | 43,112,626 | 43,112,693 | 68 | + | Simple Repeat | (TA)n |
| chr17 | 43,112,799 | 43,113,102 | 304 | - | Alu | AluSp |
| chr17 | 43,113,362 | 43,113,666 | 305 | - | Alu | AluSc8 |
| chr17 | 43,113,801 | 43,114,087 | 287 | + | Alu | AluSx1 |
| chr17 | 43,114,087 | 43,114,231 | 145 | - | Alu | AluJo |
| chr17 | 43,114,258 | 43,114,374 | 117 | + | DTr | TcMar-Tigger |
| chr17 | 43,114,390 | 43,114,460 | 71 | - | Alu | AluYj4 |
| chr17 | 43,114,462 | 43,114,580 | 119 | - | DTr | hAT-Charlie |
| chr17 | 43,114,587 | 43,114,731 | 145 | + | L1 | L1ME4b |

(1) The sequence of Simple Repeats and Low Complexity repeats sequences are described in Column 7 and Exons are double-underlined in bold.

Figure 21, continued

| Chromosome ID | Sequence Start | Sequence End | Length (bp) | Repeat Orientation or Exon Direction | Repeat or Gene ID | Repeat Subfamily[1] or Exon Number |
|---|---|---|---|---|---|---|
| chr17 | 43,115,222 | 43,115,516 | 295 | + | Alu | AluSx4 |
| chr17 | 43,115,725 | 43,115,779 | 53 | ↑ | *BRCA1* | Exon 3 |
| chr17 | 43,115,905 | 43,115,990 | 86 | - | L2 | L2a |
| chr17 | 43,116,215 | 43,116,369 | 155 | - | L1 | L1MC5 |
| chr17 | 43,116,379 | 43,116,511 | 133 | - | Alu | AluJr |
| chr17 | 43,116,524 | 43,116,818 | 295 | - | Alu | AluSq2 |
| chr17 | 43,116,820 | 43,117,091 | 272 | - | L1 | L1MC5a |
| chr17 | 43,117,159 | 43,117,456 | 298 | + | Alu | AluSx |
| chr17 | 43,117,459 | 43,117,766 | 308 | + | Alu | AluSg |
| chr17 | 43,117,839 | 43,118,368 | 530 | - | L2 | L2a |
| chr17 | 43,118,378 | 43,118,736 | 359 | - | Alu | AluJr4 |
| chr17 | 43,118,761 | 43,119,042 | 282 | - | Alu | AluSz |
| chr17 | 43,119,185 | 43,119,285 | 101 | + | Alu | FLAM_C |
| chr17 | 43,119,383 | 43,119,577 | 195 | + | MIR | MIRc |
| chr17 | 43,120,483 | 43,120,784 | 302 | + | Alu | AluYk3 |
| chr17 | 43,120,794 | 43,121,064 | 271 | + | Alu | AluSg |
| chr17 | 43,121,093 | 43,121,402 | 310 | + | Alu | AluYm1 |
| chr17 | 43,121,404 | 43,121,712 | 309 | + | Alu | AluSp |
| chr17 | 43,121,720 | 43,121,762 | 43 | + | Simple Repeat | (AACAGAA)n |
| chr17 | 43,122,339 | 43,122,616 | 278 | - | L2 | L2a |
| chr17 | 43,122,625 | 43,122,764 | 140 | + | Alu | AluJb |
| chr17 | 43,122,764 | 43,123,081 | 318 | + | Alu | AluY |
| chr17 | 43,123,081 | 43,123,235 | 155 | + | Alu | AluJb |
| chr17 | 43,123,349 | 43,123,647 | 299 | - | Alu | AluSc5 |
| chr17 | 43,124,016 | 43,124,115 | 98 | ↑ | *BRCA1* | Exon 2 |
| chr17 | 43,124,457 | 43,124,492 | 36 | + | Low Complexity | A-rich |
| chr17 | 43,124,747 | 43,124,777 | 31 | + | Simple Repeat | (TTTTG)n |

(1) The sequence of Simple Repeats and Low Complexity repeats sequences are described in Column 7 and Exons are double-underlined in bold.

Figure 21, continued

| Chromosome ID | Sequence Start | Sequence End | Length (bp) | Repeat Orientation or Exon Direction | Repeat or Gene ID | Repeat Subfamily[1] or Exon Number |
|---|---|---|---|---|---|---|
| chr17 | 43,124,781 | 43,124,980 | 200 | - | *Alu* | *Alu*Sx |
| <u>chr17</u> | <u>43,125,270</u> | <u>43,125,483</u> | <u>212</u> | <u>↑</u> | <u>*BRCA1*</u> | <u>Exon 1</u> |

(1) The sequence of Simple Repeats and Low Complexity repeats sequences are described in Column 7 and Exons are double-underlined in bold.

CLINICAL USE OF AN *ALU* ELEMENT BASED BIOINFORMATICS METHODOLOGY FOR THE DETECTION AND TREATMENT OF CANCER

CROSS-REFERENCE TO RELATED APPLICATIONS

This non-provisional patent application replaces provisional patent application No. 62/040,481 which was filed on Aug. 22, 2014. This application is a Continuation-in-Part of patent application Ser. No. 14/154,303 that was filed on Jan. 14, 2014. A related patent application Ser. No. 14/265,413 utilizes the information obtained from this invention.

CROSS REFERENCE TO RELATED APPLICATIONS

This provisional application is a continuation of non-provisional application Ser. No. 14/154,303 filed on Jan. 14, 2014, the entire contents of which is expressly incorporated by reference herein. This provisional application provides more specificity to claim 18 of non-provisional application Ser. No. 14/154,303. This revised patent application will then include Ser. No. 14/154,303 as a reference patent that is referred to in non-provisional application Ser. No. 14/265,413 filed on Apr. 30, 2014.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

1. Field of Invention

The present invention generally relates to the field of human genetics and applies to a medical benefit derived from a bioinformatic prediction of DNA damage at one or more cancer-linked regions of the genome. Monitoring of an individual for damage at a (these) cancer-linked region (regions) of instability can be used as a biomarker (biomarkers) for the early detection and subsequent treatment of cancer.

2. Description of the Related Art

Cancer is recognized as a disease of the genome {1-3}- (Visvader 2011; Yates and Campbell 2012; Garraway and Lander 2013). An estimated 80% of mutations in the DNA of cancer cells appear to be unrelated to the uncontrolled cell growth associated with the cancer phenotype. These non-cancer related mutations appear to be innocent bystander mutations which likely occurred by the same DNA damaging processes that generated the cancer phenotype {4}- (Greenman et al 2007). These passenger mutations vary not only between cancers of different tissue types, but also between cancers of the same tissue type. The repeated occurrence of mutations within a small subset of less than five percent of human genes in cancers permits identification of these potential cancer-linked genes as targets for further examination as potential drivers of cancer. Cancer driver mutations represent the subset of mutations that collectively impart the phenotype of unregulated growth to cancer cells {5&6}-(MacConaill and Garraway 2010; Forbes et al. 2011).

As discussed in detail in patent application Ser. No. 14/154,303, Alu elements are the most commonly repeated sequence in the human genome and are frequently linked to human genome instability. The human Alu element population constitutes 10.6% of our DNA. Over one million Alu elements are present in the human genome. These elements are present in statistically equivalent numbers in both positive and negative orientations {7}-(Cook et al. 2011). Both by new insertions into the genome and by their interactions with each other (post-insertion), Alu elements have been associated with various human genetic diseases including cancer {8-11}-(Deininger and Batzer 1999; Hedges and Deininger 2007; Konkel and Batzer 2010; Cook et al 2013).

Alu-Alu interactions have been linked to human DNA damage in the form of complex genome rearrangements as well as deletions, duplications and inversions within the human genome {12-15}-(Jurka et al. 2004; de Smith et al. 2008; Lee et al. 2008; Lupski 2010). Within the past 15 years over 100 studies have associated Alu elements with human DNA deletion-associated syndromes, cancer and other diseases. A selected list summarizing 12 of these studies is provided in FIG. 1 {11}-(Cook et al. 2013).

Hundreds of occurrences of deletions in the human genome have been identified that have been mediated by Alu elements. This provides strong support for the view that Alu elements are significant sources of human genome instability {16}-(Sen et al. 2006). Furthermore, several studies have identified inverted Alu elements as sources of human genome instability {17, 18, 7, 11, 19}-(Lobachev et al. 2000; Stenger et al. 2001; Cook et al. 2011; Cook et al. 2013, Kitada et al. 2013).

Alu elements and/or their fragments are commonly found at the boundaries of human structural variation {20-21}- (Kidd et al. 2010; Cooper et al. 2014). Many of the Alu constructs located at these structural variation breakpoint junctions exist as chimeric Alu elements. Chimeric Alu elements are formed as a composite construct of two older Alu elements. It is putatively accepted that most chimeric Alu elements are formed by non-allelic homologous recombination (NAHR) between two direct oriented Alu elements {16,22}-(Sen et al. 2006; Jennes et al. 2011). Significantly, other human repeat sequences such as LINE1, LINE2 and LTR elements have also been found at the breakpoint junctions of human structural variation {13-15}-(Korbel et al. 2007; Han et al. 2008; Prada and Laissue 2014).

Two closely related classes of human highly repetitive elements are microsatellites and minisatellites. Both microsatellites and minisatellites have been found to be associated with genome instability {26-29}-(Boland et al. 1998; Nawroz-Danish 2004; Ananda et al. 2014; Weitzel et al. 2000). These DNA elements are composed of small repeating groups of nucleotide bases. Microsatellites are groups of 2-9 repeating nucleotides and minisatellites are repeating groups of 10-60 nucleotide bases. The repeating length distinction between these two groups is arbitrary. A similar, but simpler type of repeat is primarily composed of one or two nucleotide bases. This construct is classified as a "Low_complexity" repeat in the RepeatMasker output in the UCSC Table Browser (http://www.genome.ucsc.edu/cgi-bin/hgTables). As with microsatellites and minisatellites, the repetitive sequences within Low_complexity repeats are also suspected of being associated with genome instability {30}-(Willams et al. 2014).

Finally, a recent study (since the submission dare of the provisional application for this application) has noted that a correlation exists in the human genome between long inverted repeats, deletion size and distance from breakpoints. Unfortunately, this study only used a sample size of 109 deletions and therefore had limited prediction value {31}-(Aygun, 2015). This patent uses a sample size of over 100 million (total Alu pairs in the human genome) and utilizes the absence of inverted Alu pairs (as compared to direct Alu pairs), rather than deletions, to derive its genome damage prediction algorithms. This large sample size permits the development of very precise algorithms for the estimation of genome instability arising from interactions of inverted repeats.

SUMMARY OF THE INVENTION

In addition to the inverted Alu-Alu interactions claimed in application Ser. No. 14/154,303, this non-provisional patent application claims the inclusion of all human inverted repetitive element pair interactions in estimating human genome instability. The collective inverted repetitive element pair interactions within a repetitive element landscape may be used together to construct an algorithm for the estimation of the genetic instability at one or more given cancer-linked regions of the genome. This patent also claims that each type of inverted pair (such as L1-L1, Alu-L1 or L1-SVA inverted pairs) possesses its own unique instability (I:D ratio) profile. Each of these unique I:D ratio profiles is incorporated as part of the larger total instability algorithm. Unfortunately, some inverted pairs may be present within a repetitive element landscape that are not present in sufficient genome-wide numbers to determine their I:D ratio profile with a high degree of statistical confidence. This provisional also claims that the I:D ratio profile for rare inverted pairs can be more accurately estimated by a comparison to the I:D ratio profiles of the most similar inverted pairs which have a higher population size, and thus are capable of generating a higher statistical confidence.

FIG. 2 in this application provides an overview of eleven different classes of human repetitive elements. Collectively, these elements account for 48.8% of the human genome sequence. As can be seen from this figure, Alu elements are the most abundant repetitive element (or sequence) in the human genome. The original patent application Ser. No. 14/154,303 showed that inverted Alu elements predictably interact, and that from this predictability, algorithms can be developed to predict the relative stability of various genetic loci. Claim 18 in this same application recognized that other human inverted repetitive element pairs were also likely to interact and, therefore, could also potentially be used in the prediction of human genome instability. However, these non-Alu/Alu pair interactions were only speculated to exist and the extent of their potential for respective interactions were not quantified. This application provides the results of 36 different examinations of different combinations of human inverted repetitive element interactions. It identifies 15 new repetitive element pairs for which significant inverted interactions have been identified (in addition to the measured Alu-Alu interactions claimed in application Ser. No. 14/154,303).

Two proposed mechanisms have been suggested for inverted Alu-Alu element interactions and are provided in FIG. 3 (also shown as FIG. 10 in patent application Ser. No. 14/154,303). Each of the two mechanisms in this figure describes potential interactions of two inverted Alu elements. It is therefore conceivable that sequences of similar homology could also catalyze interactions between the different repetitive elements described in FIG. 2. Using a similar approach to that which was used with the measurement of Alu-Alu interactions, the genome-wide interactions for multiple two-element combinations of human repetitive elements were examined. Several new repetitive element interactions were identified and are claimed in this provisional application. The results of this examination are shown in FIG. 4. It should be noted that some of these interactions are between different elements, such as the interaction between LINE1 (L1) and Alu elements. The identification and quantification of these interactions lends further support to studies that report that sequences of common microhomology are potential sources of human genome instability {32-35}-(Kitada and Yamasaki 2007; Boone 2011; Verdin et al. 2013; Ottaviani et al. 2014).

This non-provisional application claims the use of all inverted repetitive DNA elements of similar homology (10 bp and larger with 50 percent homology) in the use of bioinformatic methods for assessing the relative likelihood of genomic damage within a cancer-linked region of the human genome. Assessment of a cancer-linked region of the genome must include the stability of the flanking DNA upstream and downstream (5' and 3') of the cancer-linked region of interest. This is because the instability within these flanking regions may result in genomic damage that is large enough to extend into the cancer-linked region that is being evaluated. This non-provisional application therefore claims that proper evaluation of the stability of a cancer-linked region of the genome must include not only the specific cancer-linked region of the genome, but also the ten million base pair flanking regions both upstream (5') and downstream (3') of the cancer-linked region being evaluated. These inverted DNA elements may include any homologous (10 bp and larger with 50 percent homology) combination of SINEs, LINEs, LTR retrotransposons, DNA transposons, satellite DNA, low complexity DNA, genes and pseudogenes, duplicated DNA and other rare inverted repetitive sequences.

BRIEF DESCRIPTION OF THE DRAWINGS

FIG. 1 provides a summary of selected articles that identify Alu-Alu interactions as the source of deletions in human DNA which resulted in disease phenotypes.

FIG. 2 provides an overview of 11 human repetitive elements that collectively constitute an estimated 48.8 percent of the human genome sequence.

FIG. 4 describes the results of 36 different genome-wide examinations of the major repetitive element pair interactions within the human genome. These interactions were determined by the measurement of the genome-wide inverted:direct pair ratio (I:D ratio) for each respective repetitive element pair for Pair Sequence Numbers (PSN) 11 through 50.

FIG. 5 describes the characterization of various Alu-Alu pairs by the parameter described by the term, APSN (Alu Pair Sequence Number). The similar term PSN (Pair Sequence Number) is used to describe the pair types of repetitive element pairs.

FIG. 21 illustrates the repetitive elements described in FIG. 2 located within the BRCA1 gene in human genome assembly, hg38.

DETAILED DESCRIPTION OF THE INVENTION

Figure 3:
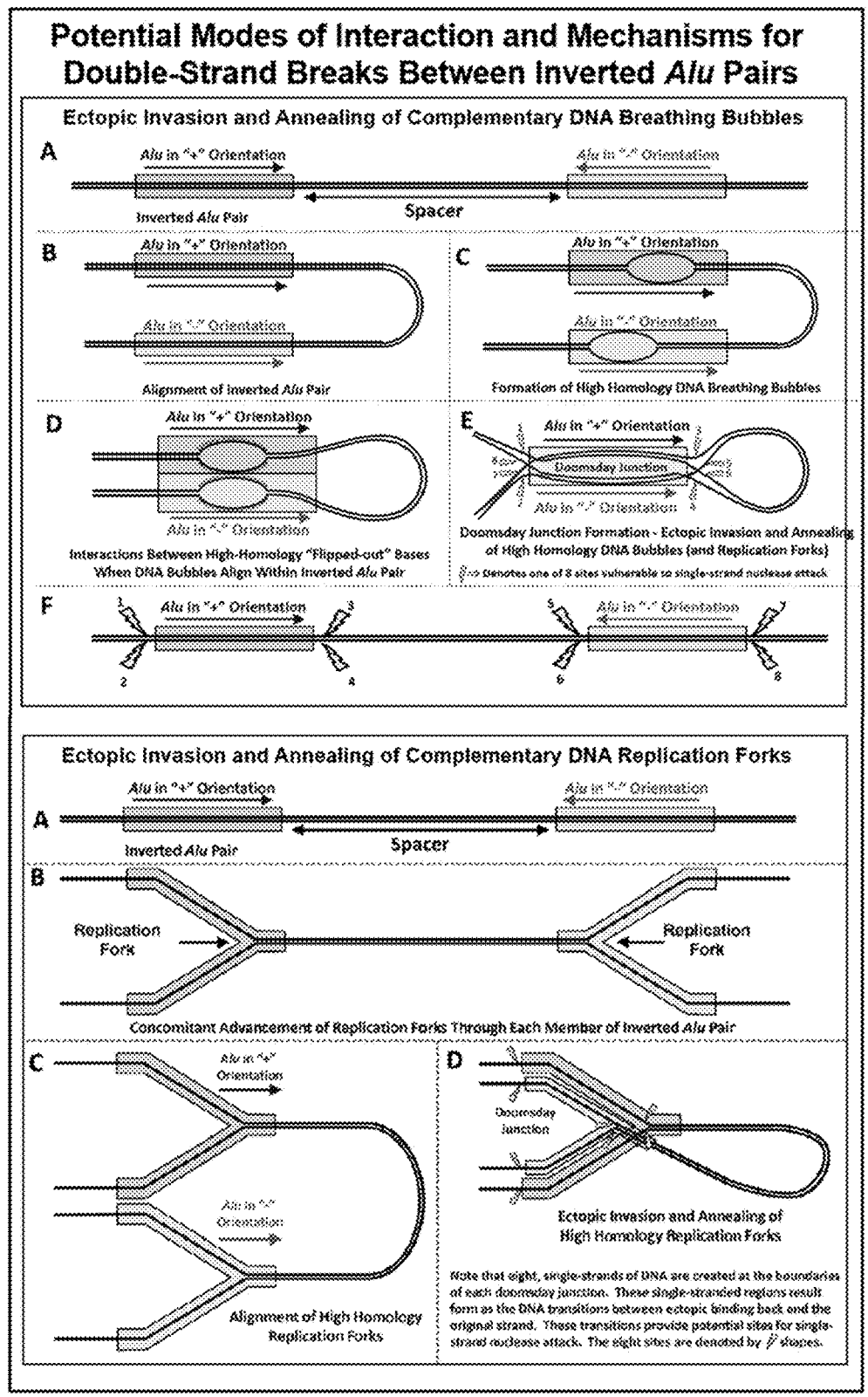
FIG. 3 illustrates two different mechanisms for Alu-Alu interactions which could result in human genome instability.

During the early part of the past decade it was commonly believed that the variation between the genomes of two randomly chosen humans was no greater than 0.1% {38}-(Jorde and Wooding 2014). This notion has been dispelled. Human-to-human genome variation strongly suggests that the human genome is much more unstable than has been previously recognized {36-37}-(Wheeler et al. 2008; Genomes Project et al. 2012). A recent study of 79 humans revealed that almost 2 million different insertions and deletions exist between the genomes of these individuals {39}-(Mills et al. 2011). A total of 1,447 copy number variable regions have been identified between humans and have been estimated to encompass 12% of the genome {40}-(Redon et al. 2006). The recent long-read sequencing of a haploid hydatidiform mole genome provides further evidence of significant human-to-human genome variation. Only 93.8% of these longer reads from this haploid genome sequence aligned with the human reference genome {41}-(Chaisson et al. 2015). Furthermore, even identical twins have been shown not to be genetically identical {42}-(Bruder et al. 2008).

Along with this new knowledge of high human-to-human genetic variation is the recent common agreement that cancer is a disease of the genome {1-3}-(Visvader 2011; Yates and Campbell 2012; Garraway and Lander 2013). Supporting the view that human genetic mutation can arise, not just over millions of years, but also within the lifetime of an individual is the observation that a colorectal tumor from a 90-year old patient typically contains approximately twice as many mutations as a similar tumor in a 45-year old patient {43}-(Vogelstein et al. 2013). Furthermore, a single-cell analysis of neurons from three individuals found that 41% (45 out of 110 neuron cells) contained deletions larger than the studies lower detectable limit of genome variation of three megabases {44}-(McConnell et al. 2013). Further examination of this data reveals that 32 of the 110 neuron cells had deletions; and 19 of the neuron cells had more than one deletion. One neuron had 20 megabase sized deletions! This data is consistent with the cancer model that genome instability begets genome instability. If the smallest deletion in each patient was the first deletion, then the largest initial deletion was 7.65 megabases. This finding is the basis for the claim that genomic instability can arise from within the ten megabase flanking regions upstream and downstream (5' and 3') of a cancer-linked region of the genome.

The recognition of the mutational heterogeneity within tumors adds additional support for the view that the human genome is unstable. Samples from the same tumor often reveal different sets of mutated genes driving the same cancer {45,43,46-50}-(Burrell et al. 2013; Vogelstein et al. 2013; Heidary et al. 2014; Lohr et al. 2014; Ricketts and Linehand 2014; Zhang 2014; Allison and Sledge 2015). This finding suggests that tumors are continually evolving. Consequently, the only certain common genetic biomarker within a tumor is the gateway mutation that initiated the original development of the pre-cancerous cell, which eventually developed into the tumor phenotype. This initiating genomic disruption may not provide a neoplastic advantage to the cell, but instead may only impart inherent genome instability that may eventually result in disrupting the coding regions of genes related to cellular proliferation. The mutation(s) associated with the gatekeeping mutation are the only common genetic biomarker that exists for all of the cells within a given tumor.

The ability to predict and thus anticipate human genomic instability prior to its occurrence could permit cancer to be prevented before it strikes. This approach to health has been demonstrated with the prevention (rather than curing) of contagious diseases such as polio and small pox. However, acquiring the ability to prevent cancer will require a fundamental understanding of the mechanisms that drive human genome instability. Gaining the required level of understanding is difficult outside of carefully controlled laboratory conditions. This is because the sequences catalyzing human genome instability are often destroyed during the DNA damaging event. This leaves only the breakpoint associated with DNA repair as evidence of the genome disruption. Following this repair, few genomic clues remain for identification of the genetic sequence that initiated the original instability.

Figure 10:
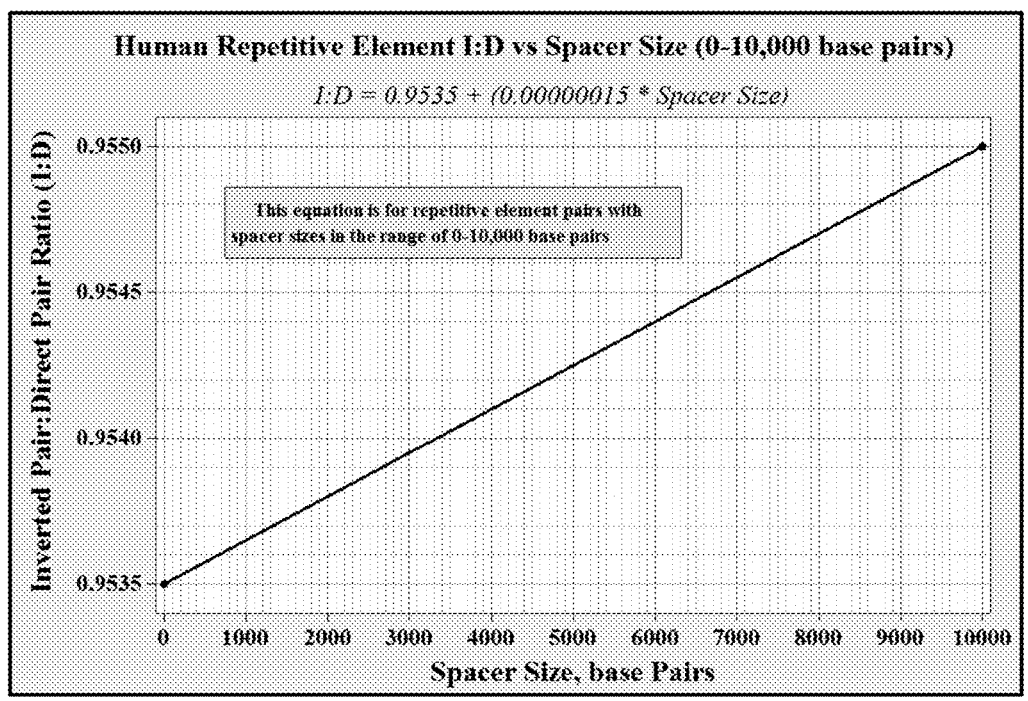
FIG. 10 illustrates the basis for the math model for non-clustered Alu-Alu pair I:D ratios within the spacer size range of 1-10,000 base pairs. This is one of three curves that collectively describe the dashed line in FIG. 9. This application of this model is shown in Table 1 of Example 1.
Figure 11:
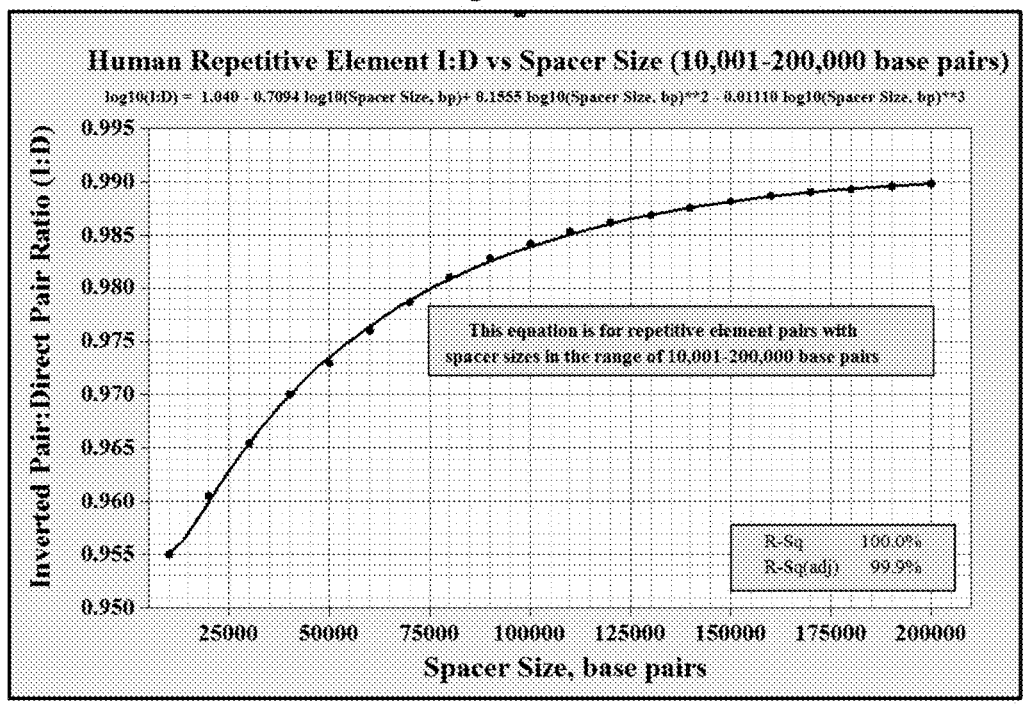
FIG. 11 illustrates the basis for the math model for non-clustered Alu-Alu pair I:D ratios within the spacer size range of 10,001-200,000 base pairs. This is one of three curves that collectively describe the dashed line in FIG. 9. This application of this model is shown in Table 1 of Example 1.
Figure 12:
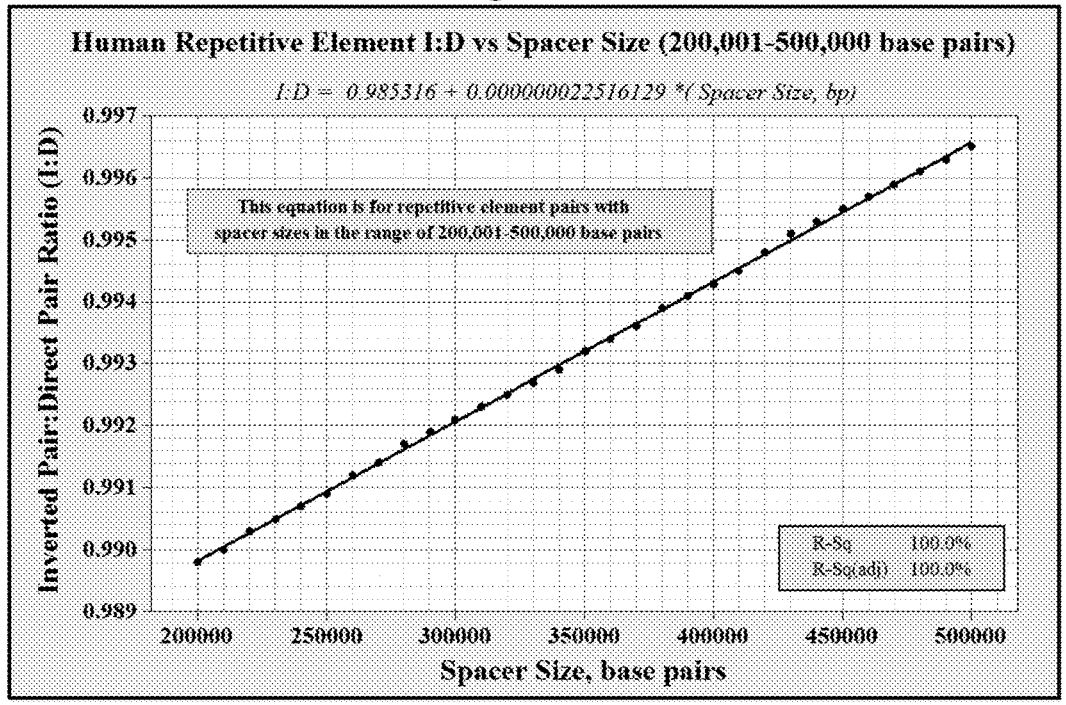
FIG. 12 illustrates the basis for the math model for non-clustered Alu-Alu pair I:D ratios within the spacer size range of 200,001-500,000 base pairs. This is one of three curves that collectively describe the dashed line in FIG. 9. This application of this model is shown in Table 1 of Example 1.
Figure 13:
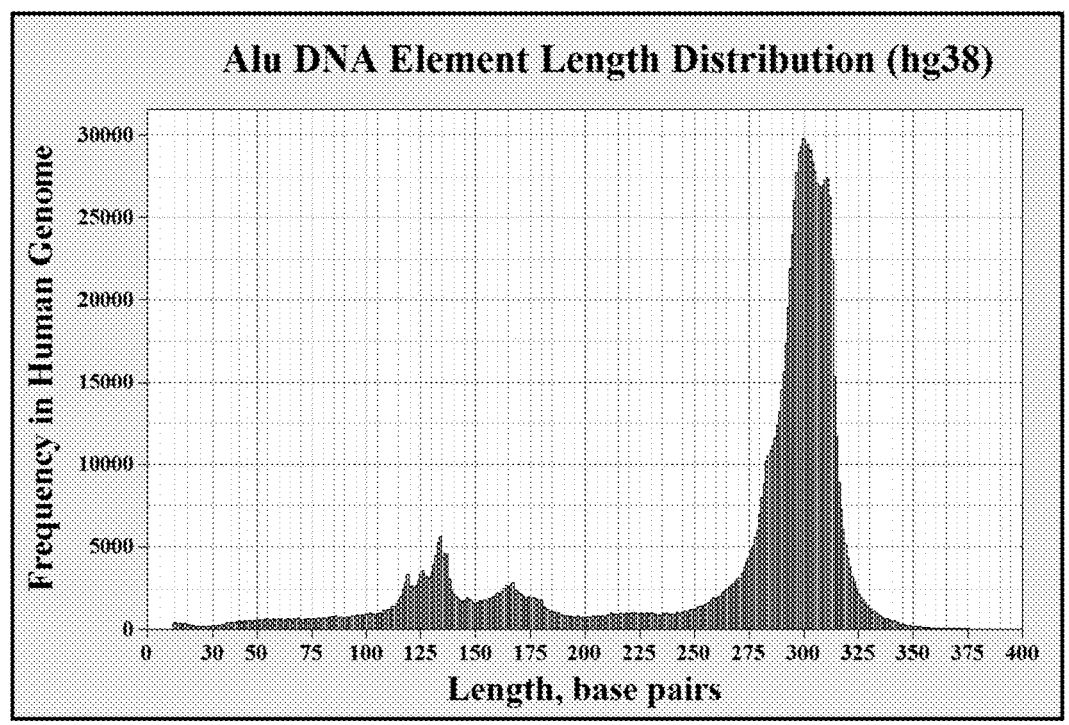
FIG. 13 illustrates the size distribution for the human Alu element population in human genome assembly, hg38.
Figure 14:
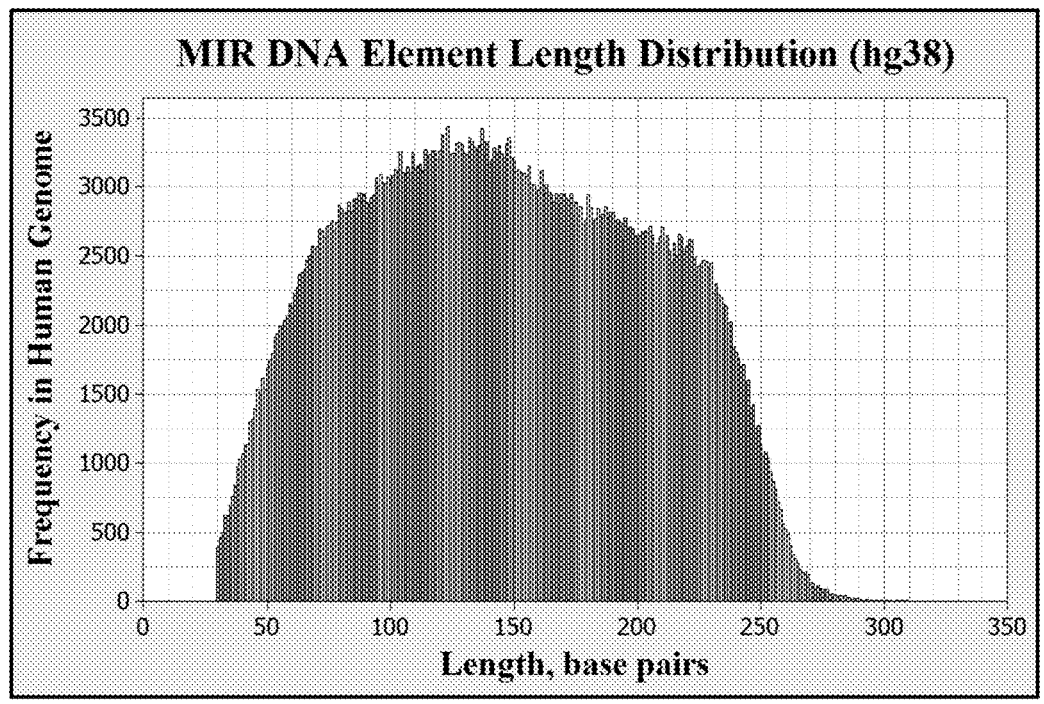
FIG. 14 illustrates the size distribution for the human MIR element population in human genome assembly, hg38.
Figure 15:
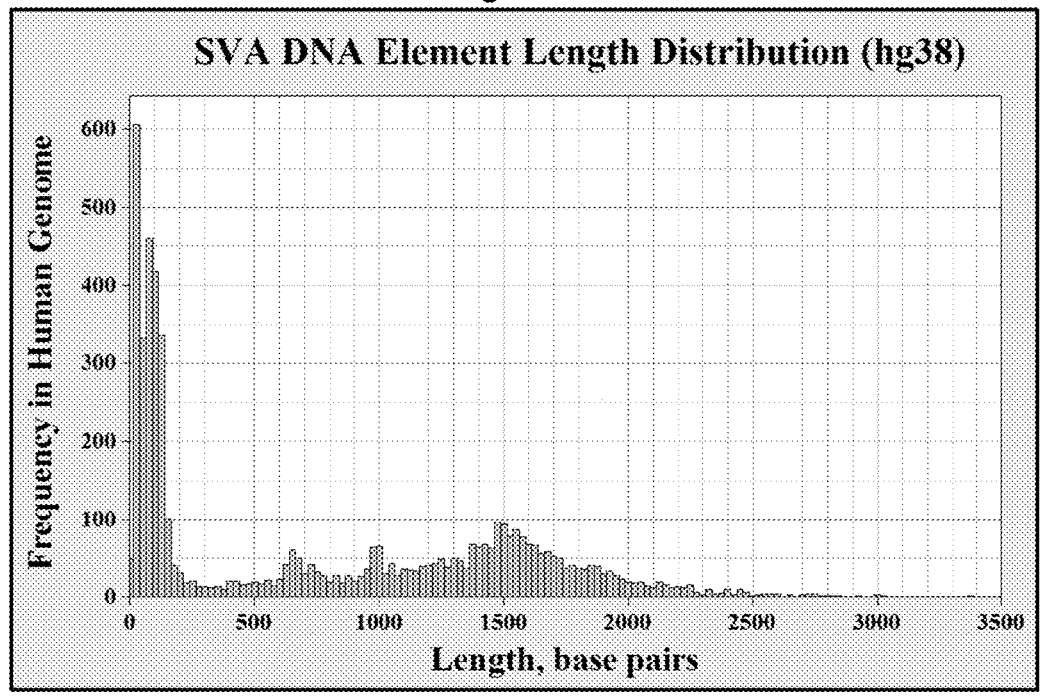
FIG. 15 illustrates the size distribution for the human SVA element population in human genome assembly, hg38
Figure 16:
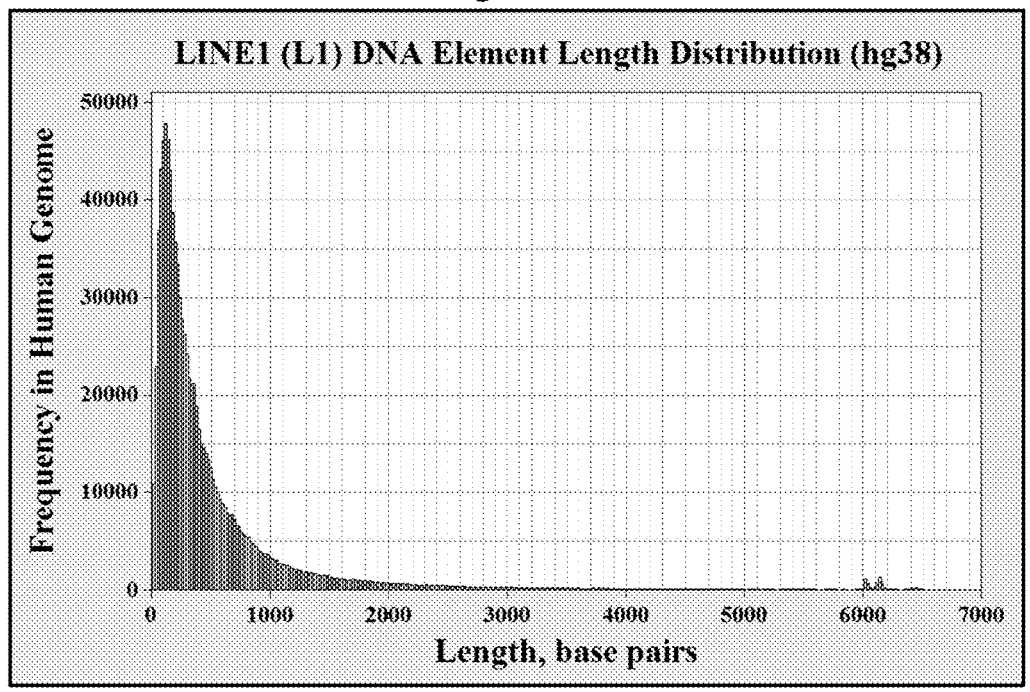
FIG. 16 illustrates the size distribution for the human LINE1 (L1) element population in human genome assembly, hg38.
Figure 17:
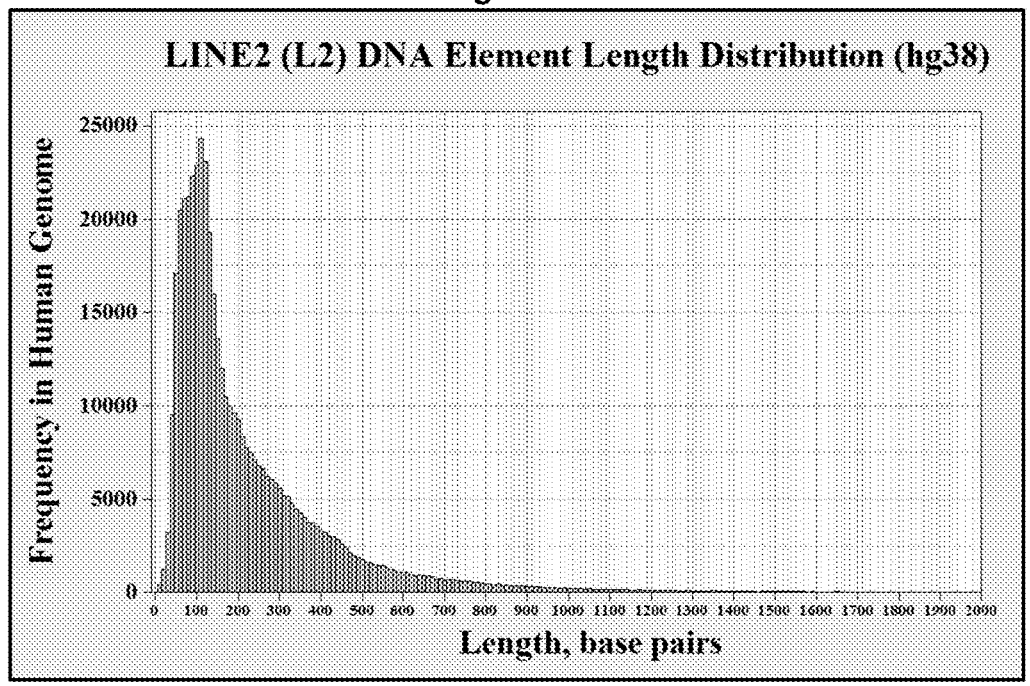
FIG. 17 illustrates the size distribution for the human LINE2 (L2) element population in human genome assembly, hg38.
Figure 18:
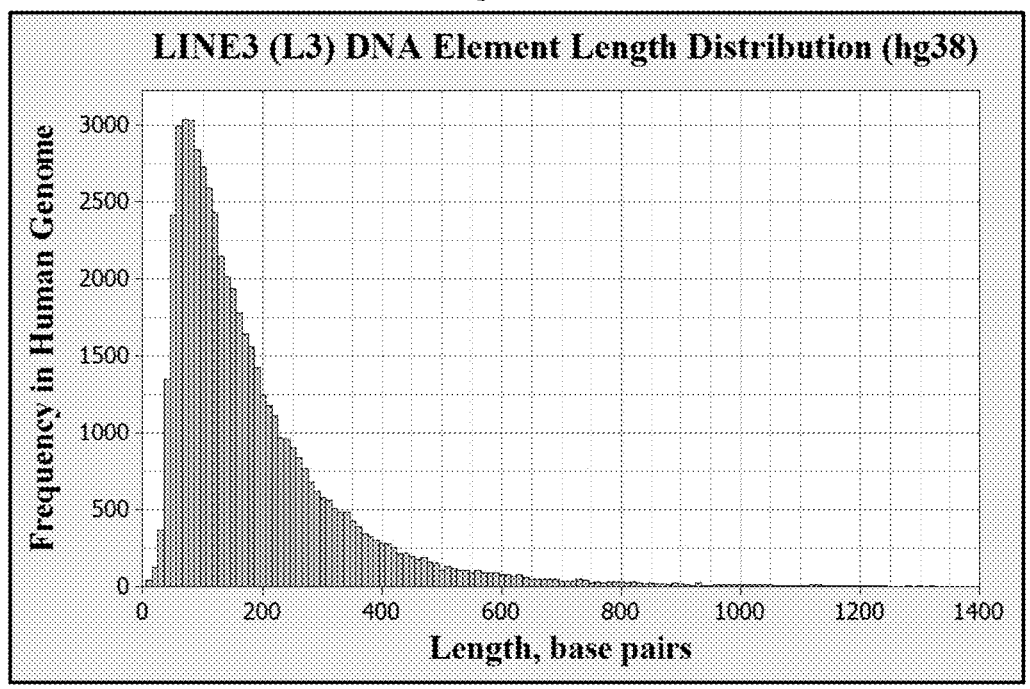
FIG. 18 illustrates the size distribution for the human LINE3 (L3) element population in human genome assembly, hg38.
Figure 19:
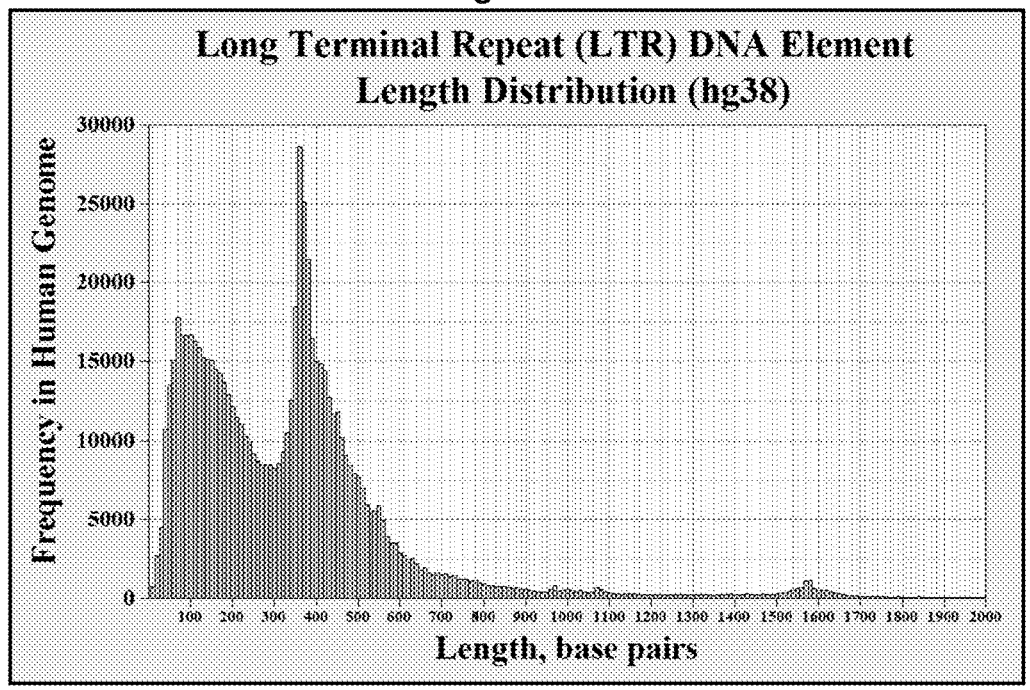
FIG. 19 illustrates the size distribution for the human Long Terminal Repeat (LTR) element population in human genome assembly, hg38.
Figure 20:
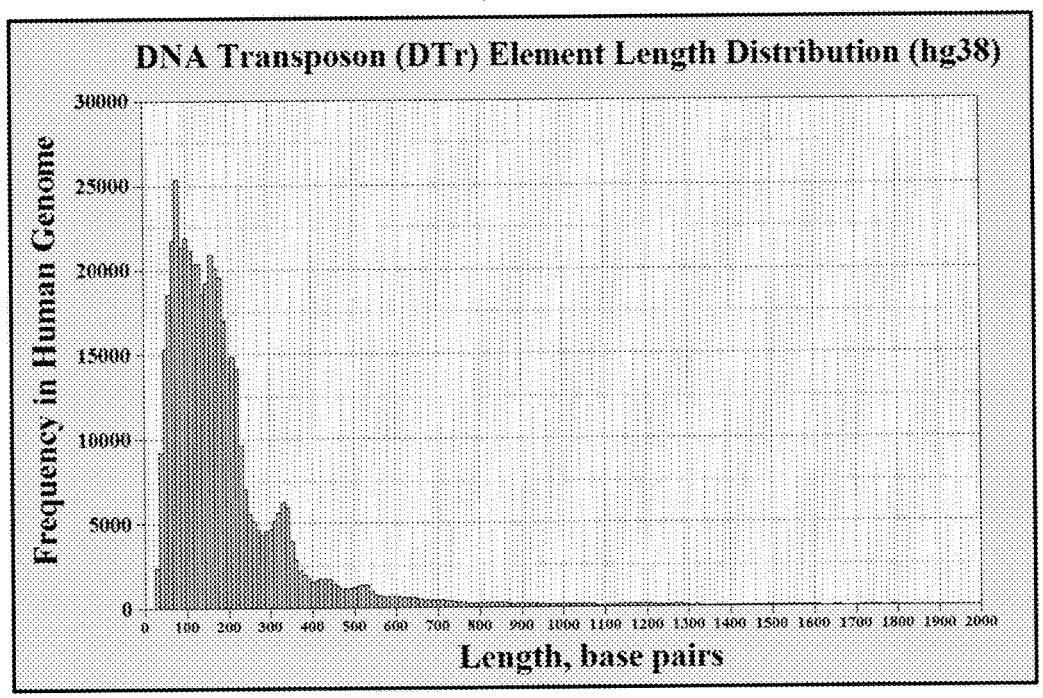
FIG. 20 illustrates the size distribution for the human DNA Transposon (DTr) element population in human genome assembly, hg38.

One clue which may relate to the mechanisms that are driving human genome instability is the imbalance in the inverted:direct Alu pair ratio (I:D ratio). This ratio has been described in U.S. patent application Ser. No. 14/154,303. This non-provisional application is a Continuation in Part of patent application Ser. No. 14/154,303. Two different instability-related mechanisms have been described which could account for the human Alu pair I:D ratio imbalance. Both of the mechanisms are illustrated in FIG. 3 (and in FIG. 10 of patent application Ser. No. 14/154,303). It is postulated that similar mechanisms may also occur between other repetitive elements present within the human genome. The activity of such mechanisms can be identified by measuring the I:D ratio of the specific repetitive element pairs being evaluated.

A study was conducted to measure the genome-wide I:D ratio for human repetitive element pairs other than Alu/Alu pairs. The repetitive elements that were analyzed in this study are the first eight repetitive elements listed in FIG. 2. The purpose of this study was to determine 1) if other repetitive element pairs were also sources of human genome instability (as determined by an I:D ratio below unity) and 2) the relative instability of these different repetitive element pairs as compared to the Alu-Alu pair I:D ratio, which was also determined in this same study as a baseline. This Alu-Alu pair baseline enables the use of the original Alu-Alu pair I:D algorithms in estimating the I:D ratios for other inverted pairs (see Example 1). These original Alu-Alu pair I:D algorithms which were developed in non-provisional patent application Ser. No. 14/154,303. The genome-wide size distributions for these eight mobile elements are provided in FIGS. 13-20. These size distributions clearly indicate that all of these elements have undergone significant fragmentation. This level of mobile element fragmentation supports the view that the human genome is inherently unstable.

It has been previously shown that inverted Alu elements can interact with one another down to lengths as small as 30 bp (Cook et al. 2013). This demonstrates that the interaction of different repetitive elements is possible if they share high homology sequences as short as 30 base pairs (bp) in length. The ability of such short Alu pairs to interact suggested that this study should include the evaluation of unmatched mobile elements (such as Alu-L1 mobile element pairs). This interaction between unmatched repetitive element pairs might be possible if, for instance, both repetitive elements contain a polyA tail. Once the ectopic DNA conformation known as a doomsday junction is formed between two different repetitive elements (FIG. 3), it is possible for mismatch repair proteins to increase the homology between these two repetitive elements. If the resolution of the doomsday junction by single-strand nucleases does not result in a double-strand break (see diagrams E and F in the top pane of FIG. 3), the resultant increased homology (because of mismatch repair) between these two elements will further increase the likelihood of their future interaction. Instances of homology increasing Alu-Alu interactions are supported both by 1) gene conversion events which convert an older Alu subtype into a more recent subtype and 2) by the homogenization of neighboring Alus {51-54}-(Kass et al. 1995; Roy et al. 2000; Zhi 2007; Aleshin and Zhi 2010). It should finally be noted that the formation of DNA duplications are also possible with the formation of doomsday junctions at replication forks (bottom pane of FIG. 3). This ectopic DNA conformation of two complementary DNA replication forks coupled with the assembled replication proteins could result in the duplication of DNA that had previously been replicated. This DNA duplication could occur if the replication fork proteins reassembled onto one of the ectopic DNA strands that are inserted into the replication fork during the formation of a Doomsday Junction (Cook et al. 2011).

FIG. 4 presents the results of the mobile element interaction (I:D ratio) study. The genome-wide I:D ratios for 36 different human mobile element pairs are presented within the grid of this figure. Also, to avoid clustering biases, the I:D ratio is only reported for those elements that are separated by 11-50 identical elements (PSNs 11-50) (Cook et al. 2011). This decision to only report the I:D ratios of widely-spaced repetitive elements is the equivalent of only reporting Alu pair sequence numbers of 11-50 (described in FIG. 6). Using the I:D ratio of Alu-Alu elements as a baseline reference, this cautionary step, while significantly reducing the departure of the I:D ratios below unity (1.0), also insures that the detected I:D ratios below 1.0 accurately portray those mobile element pair interactions which are not confounded by clustering biases. Finally, since the population sizes of these pairing types of mobile elements vary in number, the confidence interval for each I:D ratio also varies accordingly. These confidence intervals are presented below each I:D value in the grid in FIG. 4.

Two-thirds of the total repetitive element pairs (24 of 36) evaluated in FIG. 4 possessed I:D ratios that were statistically below unity ($p<0.05$). For this study, when the I:D ratio of a selected repetitive element pair falls statistically below unity, it is considered to be a reactive pair and a potential source of genome instability. The individual I:D ratios for all 36 repetitive element pairs described in FIG. 4 are shown as shaded blocks. Note also from FIG. 4 that only five of the 24 identified interactions were between identical repetitive elements with eleven identified interactions being between non-identical elements. A low I:D ratio for non-identical repetitive elements may reflect interaction because of shared microhomology (Kitada and Yamasaki 2007; Boone 2011; Verdin et al. 2013; Ottaviani et al. 2014).

Note in FIG. 4 that the most active interaction among these 36 mobile element pairs is between L1-SVA pairs which have a genome-wide I:D ratio of 0.878 and a 95% confidence interval of 0.010 (0.868-0.888). This low (highly interactive) I:D value may reflect that L1 and SVA elements share a common region of high homology. This high homology is not entirely unexpected since both of these full length elements possess polyA tails. Also note from FIG. 4 that eight of these repetitive element pair interactions are more pronounced (lower I:D ratio) than the corresponding Alu-Alu pair interactions. Finally, note that eight of the 24 mobile element pairs I:D ratios were only slightly below unity. The remaining 16 mobile element pairs have I:D ratios below 0.99.

Use of the repetitive element pair sequence numbers, PSNs, of 11-50 in FIG. 4 (equivalent to Alu pair sequence numbers, APSNs, for non Alu-Alu pairs; see also FIG. 5 and patent application Ser. No. 14/154,303) likely results in this measured I:D ratio being higher (less interactive) than the actual overall I:D ratio. An example of this dampened I:D ratio phenomenon is that the reported I:D ratio in FIG. 4 for L1-L1 element interactions is 0.931 (PSNs 11-50), while the I:D ratio for L1-L1 interactions for PSNs 1-10 is 0.769. Note that the higher I:D ratio is associated with the PSN range of 11-50. Use of the higher PSN range, while likely understating a repetitive pair's actual interaction, also avoids confounding of the I:D ratio by repetitive element clustering bias {7}-(Cook et al. 2011). A method for correcting the I:D ratios in FIG. 4 to more accurately reflect the actual I:D ratio associated with each repetitive element pair is described in EXAMPLE 1. This method adjusts the inflated I:D ratios in FIG. 4 by normalizing them with the algorithms derived from the human Alu-Alu pair populations. EXAMPLE 1 is only one of several methods that can be utilized to estimate a more reliable I:D ratio for a human repetitive element pair by use of the human Alu-Alu pair I:D ratio. This invention claims the use of the human Alu-Alu pair I:D ratio algorithms claimed in non-provisional patent application Ser. No. 14/154,303 to estimate the I:D ratios for other human repetitive element pairs for the purpose of estimating human genome instability. The method described in EXAMPLE 1 for estimating human genome instability by the use of the collective human repetitive DNA structure is the centerpiece of this invention.

It should be also be noted that the genome-wide density of a given repetitive element can vary significantly from that element's density in gene dense regions of the genome. For instance, while Alu, SVA, L1 and LTR elements occupy human genome-wide sequence fractions of 10.6%, 0.15%, 17.3% and 9.1%, respectively, their density within and ±10,000 bp flanking landscapes of 52 cancer-linked genes is 17.8%, 0.24%, 10.7% and 2.1%, respectively. Note that the percentage of sequence for Alu and L1 elements effectively swap places when comparing their sequence percentages in cancer-linked regions of the genome to their genome-wide sequence percentages. The sequence fraction ratios of Alu, SVA, L1 and LTR elements with these cancer-linked genes landscapes compared to their genome-wide sequence fractions is 1.7, 1.7, 0.6 and 0.3.

Figure 6:
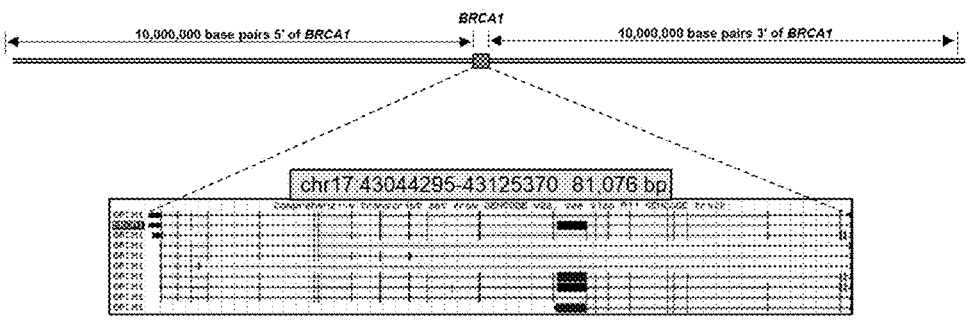
FIG. 6 illustrates the size of a typical repetitive element landscape within the human genome. BRCA1 is used in this example. This landscape contains the repetitive elements which may interact and result in genomic damage to this cancer-linked gene.

FIG. 21 describes the position of various repetitive elements within the introns of BRCA1, the human early onset breast cancer type 1 susceptibility gene in the most recent human genome assembly, hg38. The exons of BRCA1 are also shown in bold and double underlined. These repetitive elements as well as those repetitive elements residing within the ten million base pair regions immediately upstream and downstream (5' and 3') of BRCA1 comprise the repetitive element landscape for this gene. Using the most recent human genome assembly, hg38, the UCSC genome browser reports that 44,408 repetitive elements reside within the BRCA1 landscape (FIG. 6). It is the unique repetitive landscape associated with each cancer-linked region of the genome that is used in this invention to estimate its genomic instability. Many of these landscapes will likely be unique to each patient. The comparison of the instability estimates for the various cancer-linked regions of a patient's genome permits the most unstable regions to be identified. This information is then used for developing the clinical methodologies described in patent application Ser. No. 14/265, 413.

Before the present invention is further described, certain terms employed in the specification and claims are collected here. These definitions should be read in light of the remainder of the disclosure and understood by a person of skill in the art. Unless otherwise defined, all technical and scientific terms used herein have the same meaning as commonly understood by a person of ordinary skill in the art.

A. Definitions

The terms "3'" and "5'" refer to the upstream and downstream directions from a genomic reference point, respectively.

The term "APSN" is an abbreviated form of "Alu Pair Sequence Number" and refers to the sequential number of Alu elements separating the first Alu in an Alu pair from the second Alu element in the same pair. The Alu pair sequence number can also be defined as the "n+1" number of Alu elements within the spacer sequence separating an Alu pair (see FIG. 5).

The term "autonomous" refers to a type of mobile element that contains the coding sequences for enzymes that when transcribed and translated, enable the mobile element to become capable of effecting its own insertion into the genome.

The term "bp" refers to a genetic distance or length of a DNA sequence in base pairs.

The term "breakpoint" refers to the boundary of a disrupted genomic sequence of structural variation. This terminology can be misleading, as breakpoint does not describe the original break in DNA sequence, but only the locus of the final repair. Thus, breakpoint only identifies the repair point.

The term "central Alu element" refers to an Alu element for which the stability is being estimated. Each Alu element can potentially interact with 220 of its immediately flanking Alu neighbors (APSN range of −110 to +110, see FIG. 5). In other words, the "central Alu element" is therefore the common Alu that is always one of the two Alu elements involved in each of these 220 potential interactions.

The term "chimeric Alu element" refers to the recombination product of two older Alu elements. These recombined Alus are commonly found at the sequence breakpoints of structural variation, and are putatively accepted as being formed by non-allelic homologous recombination (NAHR) between two direct oriented Alu elements.

The term "confidence interval" refers to the margin of error, which provides a 95% certainty of the value presented ($p<0.05$).

The term "direct Alu pair" refers to Alu pair with the two Alu elements in the same orientation. The term "inverted Alu pair" refers to an Alu pair with the two Alu elements in opposite orientation.

The term "doomsday junction" (or DDJ) refers to the DNA conformation resulting from the ectopic invasion and subsequent annealing of two high-homology DNA breathing bubbles or replication forks. Such interactions can potentially occur when double-stranded DNA is separated, forming two single strands of DNA. Single strands of DNA occur in DNA breathing bubbles and replication forks {55}-(Fogedby and Metzler 2007). Such high-homology interaction events might arise when DNA breathing bubbles or replication forks pass through two inverted Alu elements. The hypothesized doomsday junctions formed by inverted Alu element interactions between DNA breathing bubbles and replication forks are illustrated in FIG. 3 {7,11}-(Cook et al. 2011; Cook et al. 2013).

The term "DNA Transposon" refers to a DNA element that is capable, or has previously been capable of, moving within a genome through a cut and paste mechanism. No DNA transposons are known to be active in the human genome.

The term "DTr" refers to the abbreviated term "DNA Transposon" which is a mobile DNA element that moves within a genome through a cut and paste mechanism.

The term "duplication" refers to two or more regions of DNA that have been duplicated through non-mobile element duplication mechanisms. Duplicated DNA is putatively believed to occur through ectopic interactions at DNA replication forks.

The term "DSB" refers to a double-strand break in the DNA. Double-strand breaks can occur at the end of Alu elements during the resolution of doomsday junctions (FIG. 3).

The term "gateway mutation" refers to the initiating disruption to the DNA sequence in a cancer cell, which ultimately results in the cell's development into a cancer phenotype. It should be noted that this initiating disruption may not confer any growth advantage to the cancer cell, but may only impart genome instability that will eventually result in damage to genes that control cellular proliferation.

The term "homologous" refers to the two or more similar nucleotide sequences. Homologous regions of DNA are often less than 100 identical. However, random DNA sequences share approximately 25 percent homology because of the four nucleotide bases that make up DNA.

The term "hydatidiform mole" is a rare growth than can occur during an abnormal pregnancy. Some of these cysts contain only DNA from sperm, and thus can be a source of multiple copies of amplified haploid DNA.

The term "I:D ratio" refers to the ratio of the number of inverted human Alu pairs to the number of direct oriented human Alu pairs within a genomic region of interest. The I:D ratio is not a singular number, but is rather an I:D ratio profile which varies as a function of spacer size, clustering state, homology and PSN (pair sequence number), and is a measure of the stability of an inverted pair. A region of interest can refer to a genomic region as large as the entire human genome.

The term "indel" refers to a DNA sequence that is present in one genome, but is absent from another. With only two genomes with which to compare, it cannot be known whether the extra DNA sequence resulted from an insertion in one genome or a deletion in the other. This conundrum of the origin of this sequence is therefore expressed as a conjugation of the two words insertion and deletion.

The term "intervening sequence" refers to the DNA sequence separating the two repetitive elements that make up a repetitive element pair.

The term "LTR" refers to the abbreviated term that describes "Long Terminal Repeat", which is a class of repetitive element in the human genome.

The term "Low complexity" DNA is a region of DNA that is predominantly composed of one or two nucleotides.

The term "microsatellite" refers to a repeating nucleotide sequence of approximately 10-60 base pairs.

The term "minisatellites" refers to a repeating nucleotide sequence of approximately 2-9 base pairs.

The term "LINE element" is an abbreviated form of "Long Interspersed Elements". LINE elements represent the largest family of repetitive elements in the human genome. A full length LINE element is approximately twenty times longer than a full-length Alu element. Therefore, while LINE elements occupy a larger sequence fraction of the human genome than Alu elements, Alu elements are present in a larger number of copies in the human genome.

The term "l" is an abbreviated form for LINE1 elements (see FIG. 2).

The term "L2" is an abbreviated form for LINE2 elements (see FIG. 2).

The term "L3" is an abbreviated form for LINE3 elements (see FIG. 2).

The term "LINE1" refers to the only member of the LINE element family that is active in the human genomes. LINE1 elements are the only autonomous retrotransposons in the human genome.

The term "LINE2" refers to a member of the LINE element family that is inactive in the human genome.

The term "LINE3" refers to a member of the LINE element family that is inactive in the human genome.

The term "megabase" refers to one million base pairs of genome sequence.

The term "mobile element" refers to a DNA sequence that is capable, or has been capable of moving within a genome.

The term "neoplastic" refers to a tissue phenotype characterized by abnormal cell growth.

The term "nonautonomous" refers to a type of mobile element that does not contain the coding sequences for enzymes to effect their own insertion into the genome. These mobile elements must utilize the enzymatic machinery of other autonomous mobile elements to affect their own insertion into the genome.

The term "orthologous" refers to genes that diverge following a speciation event.

The term "polyA tail" refers to a poly adenine tail that are often present in Alu, LINE1 and SVA retrotransposons, which are the only three mobile elements that are known to be currently active in the human genome.

The term "PSN" is an abbreviated form of "Pair Sequence Number" and refers to the sequential number of repetitive elements (of the type of repetitive elements which make up a repetitive element pair) separating the first repetitive element in the pair from the second repetitive element in the same pair. The PSN pair sequence number can also be defined as the "n+1" number of repetitive elements within the spacer sequence separating a repetitive element pair (see also FIG. 5). As an example, if the repetitive element pair that is being examined is an L1-L1 pair, then the PSN would be the "n+1" number of repetitive elements residing within the pair. If three L1 elements reside with the spacer of an L1-L1 pair, then the PSN for that L1-L1 pair would be 3+1=4. As a second example, if the repetitive element pair that is being examined is an unmatched pair that is made up of two different types of repetitive elements, then the PSN would be the "n+1" number of the second repetitive elements residing with the spacer. If this pair is a LTR-SVA pair, and the central element (see FIG. 5) is the LTR repetitive element, then the PSN of a pair would be the "n+1" number of SVA elements that reside within the spacer. It should be noted that the term APSN, Alu Pair Sequence Number was first used to describe this feature of Alu pairs in patent application Ser. No. 14/154,303. Thus the APSN is the same as the PSN for Alu-Alu pairs.

The term "repetitive element" refers to two or more repeated sequences in the human genome of 10 base pairs or longer with 50 percent sequence homology.

The term "repetitive element landscape" refers to the structure of the various repetitive elements within and flanking a region of interest within the human genome. The genomic structure within a given landscape establishes the environment where inverted repeats can potentially ectopically interact and initiate genome instability. Each region of the human genome has its own unique repetitive element landscape.

The term "retrotransposon" refers to a DNA sequence that is capable, or has been capable of movement within a genome via an RNA intermediate through a copy-and-paste mechanism. Alu, SVA and LINE1 elements are active retrotransposons in the human genome.

The term "pseudogene" refers to a processed region of a gene most often without the intronic regions of the actual gene. This suggests that the processed messenger RNA from the transcribed gene has undergone reverse transcription to DNA prior to insertion. Pseudogenes can contain the complete exonic sequence of the actual gene or only a fragment of the exonic sequence. Many pseudogenes contain polyA tails, as well as duplicated DNA, which flanked the original gene. These flanking sections of duplicated DNA are indicative of insertion by the enzymatic insertion machinery of LINE1 elements.

The term "simple repeat" refers to the UCSC terminology for a microsatellite.

The term "SVA" refers to a composite retrotransposon, which is active in the human genome. This term refers to the structure of the element, which is composed of 1) a SINE-sized fragment from an LTR Element, 2) a VNTR and 3) portions of an Alu element.

The term "spacer" has referred, in previous related provisional and non-provisional patents, to the sequence separating the two Alu elements in an Alu pair. In this non-provisional patent application, this term is now used to refer to the DNA sequence separating other repetitive element pairs (including Alu-Alu pairs). Other repetitive elements may reside within this spacer sequence.

The term "transposon" refers to a mobile DNA element that moves in the genome via a cop-and-paste mechanism. It should be noted that older research articles have often used this term to include retrotransposons. However, this term is currently most often used to refer only to those DNA elements that mobilize through a cut-and-paste mechanism. This second definition is used in this non-provisional patent application.

The term "VNTR" refers to a region of DNA which contains a variable number of tandem repeats.

B. Examples

The described embodiments of this invention are shown in EXAMPLE 1 and EXAMPLE 2 below, represent the preferred embodiments of the present invention. However, it is to be understood that those skilled in the art of genetics, math and statistics can modify the various methodologies associated with these embodiments of the invention without departing from its spirit. These examples are intended to be exemplary of the invention.

It should also be noted that once the I:D ratio of a repetitive element pair is estimated, this I:D ratio can then be directly incorporated into the Alu element related algorithms claimed in patent application Ser. No. 14/154,303. Thereafter, the respective repetitive elements making up this pair can then be treated the same as an Alu element in the methodologies described in patent application Ser. No. 14/154,303. Accordingly, Example 1 describes a non-limiting method for the estimation of the I:D ratio for several different individual inverted repetitive element pair interactions. Example 2 describes a method for estimating the composite stability of a repetitive element that resides within the repetitive element landscaped described in FIG. 7.

Example 2 is intended to be a representation of the method provided in Example 1 of patent application Ser. No. 14/154,303 entitled, "A simplified estimate of the stability of one Alu element that resides within the BRCA1 Alu landscape". This example illustrates how a repetitive element is to be treated as an Alu element in the Alu-related algorithms described in patent application Ser. No. 14/154,303.

Example 1

Figure 7:
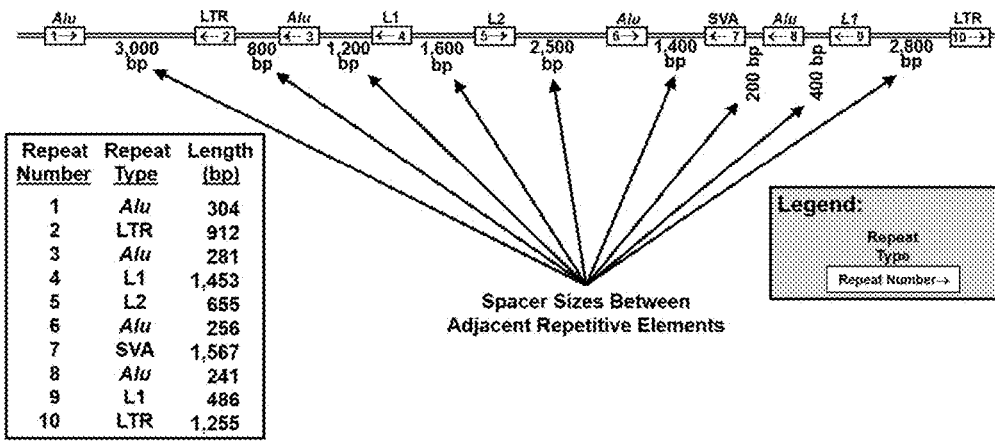
FIG. 7 illustrates a small hypothetical region of the human genome that is populated with ten selected repetitive elements. This figure is used as the basis for Example 1 and Example 2.
Figure 8:
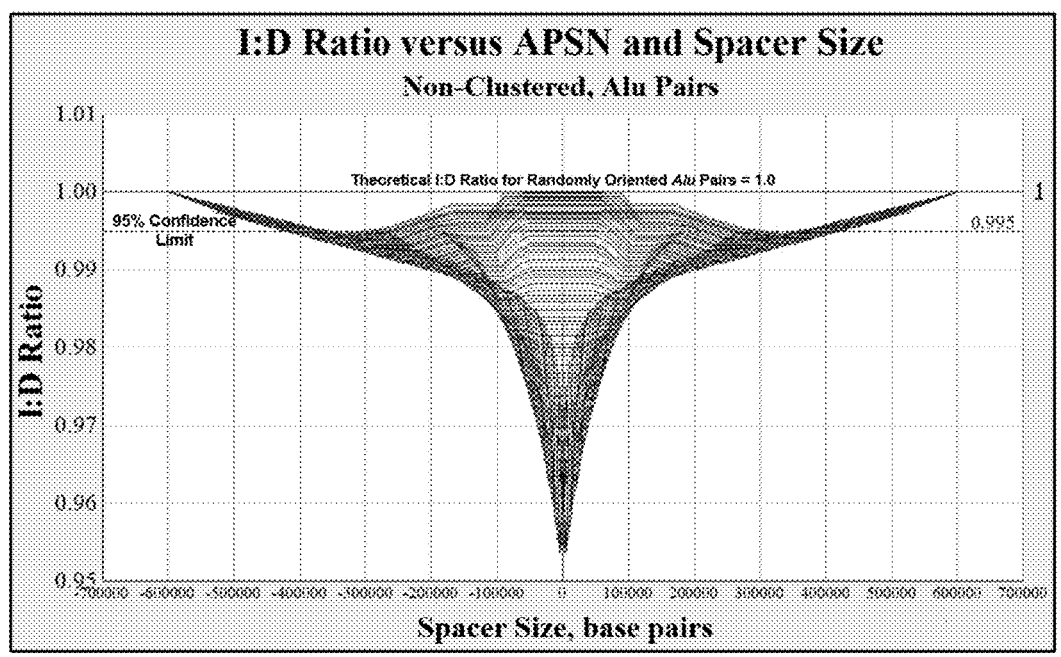
FIG. 8 is a diagram of the variation of the non-clustered Alu-Alu pair I:D ratio within the human genome for APSNs between −110 to +110 {11}-(Cook et al., 2013).

A Simplified Estimate of the Stability of One Repetitive Element (L2 Element) that Resides within the Repetitive Element Landscape Described in FIG. 7

Table 1 lists the three algorithms that describe the lowest Alu-Alu pair I:D ratios for non-clustered Alu pairs. These lowest I:D ratios are described by the dashed line on the right-hand side of FIG. 9. Since the curves (surface) in this figure are symmetrical, these three algorithms also can be used to describe the lowest I:D ratios on the left side of the surface. Example 1 is not intended to be limiting as to how the Alu-Alu pair I:D versus spacer size curves can be utilized to provide more accurate estimates of the I:D ratios for various repetitive element pairs, but is intended to be exemplary of this invention.

TABLE 1

Alu-Alu Pair I:D Estimates for Repetitive DNA Element I:D Estimates

| Spacer Size Range (Base Pairs) | Algorithms for Determining Equivalent I:D in non-Clustered Alu Elements |
|---|---|
| 0-10,000 | I:D = 0.9535 + (0.00000015 × Spacer Size) |
| 10,001-200,000 | I:D = 10^(1.040 − 0.7094 × log(Spacer Size) + (0.1555 × log(Spacer Size)$^2$) − (0.01110 log × (Spacer Size)$^3$) |
| 200,001-500,000 | I:D = 0.985316 + (0.000000022516129 × (Spacer Size)) |

A detailed description of each of the columns in Table 2 is provided below.

Column 1—A numerical description of the 45 possible repetitive element pairs which can be formed from the repetitive element landscape provided in FIG. 7.

Column 2—A named description for each of the repetitive element pairs described in Column 1.

Column 3—The I:D ratio across Pair Sequence Numbers (PSNs) for each of the repetitive pairs described in FIG. 7. The I:D ratios in this column are provided in FIG. 4.

Column 4—The relative departure from unity (1.0) of the I:D ratio for each of the repetitive pairs provided in Column 3 as compared to Alu-Alu pairs. The I:D ratio for Alu-Alu pairs in FIG. 4 (and used in Column 3) is 0.971. This relative departure from unity is described as $\mu$, where $\mu=(1-$I:D of repetitive element pair, FIG. 4$)/(1-0.971)$).

Column 5—The spacer size separating each of the 45 repetitive element pairs described in Column 2. These spacer size values are obtained by summing the various lengths of repetitive elements and the sequence lengths that separate them are taken from FIG. 7.

Figure 9:
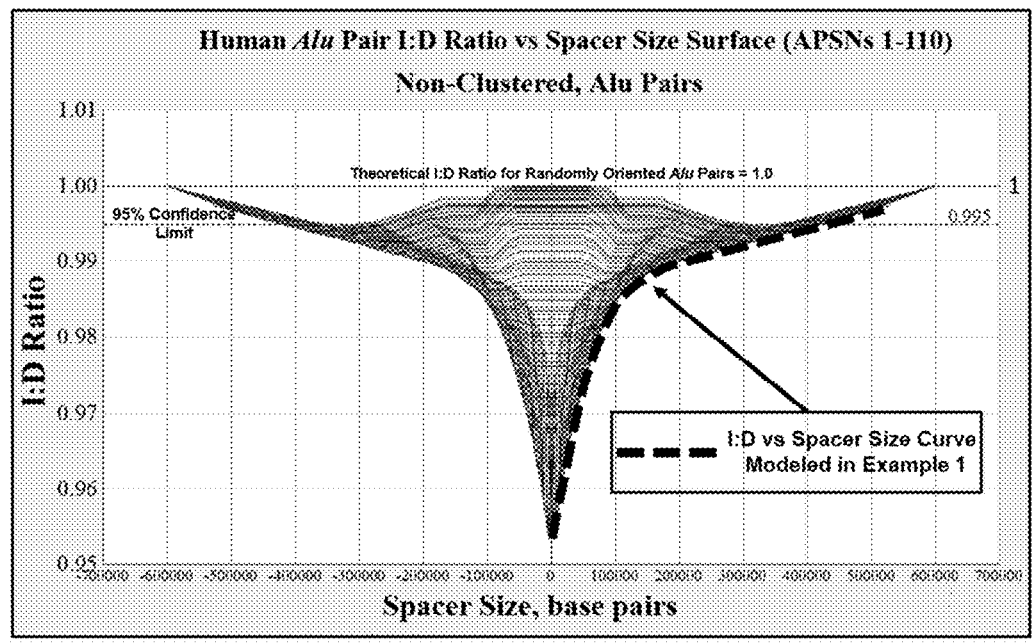
FIG. 9 is the same diagram illustrated in FIG. 8, but which also includes the Alu-Alu pair I:D ratio versus spacer size curve which is modeled in Table 1 of Example 1.

Column 6—The estimated actual I:D for Alu-Alu pairs determined from the algorithms in Table 1 which describe the dashed line in FIG. 9. This I:D value is determined for each repetitive element pair described in Columns 2 and 5. This I:D value is described as "0".

Column 7—Using the multiplier, $\mu$, provided in Column 4 and the "0" value provided in Column 6, the I:D ratio for each repetitive element pair is estimated. This estimation uses the following formula.

$$\text{I:D ratio for a repetitive element pair} = 1-((1-\tau\delta)\times\mu)$$

TABLE 2

Repetitive DNA Element Pair I:D Estimates from FIG. 7

| Repetitive Element Pairs (Numbers) | Repetitive Element Pairs (Types) | Repetitive Pair I:D for PSNs 11-50[1] | Multiplier "$\mu$" for Using Alu-Alu Pair Algorithms $(1 - I:D)/1-0.971)^2$ | Spacer Size (bp)[3] | Estimated Alu-Alu I:D "$\tau\delta$" from Table 1 | Estimated I:D for Repetitive Element Pairs $1 - ((1 - \tau\delta) \times \mu)^4$ |
|---|---|---|---|---|---|---|
| 1-2 | Alu-LTR | 0.983 | 0.586 | 3,000 | 0.9540 | 0.9730 |
| 1-3 | Alu-Alu | 0.971 | 1.000 | 4,712 | 0.9542 | 0.9542 |
| 1-4 | Alu-L1 | 0.946 | 1.862 | 6,193 | 0.9544 | 0.9151 |
| 1-5 | Alu-L2 | 0.994 | 0.207 | 9,246 | 0.9549 | 0.9907 |
| 1-6 | Alu-Alu | 0.971 | 1.000 | 12,401 | 0.9558 | 0.9558 |
| 1-7 | Alu-SVA | 0.917 | 2.862 | 14,057 | 0.9566 | 0.8758 |
| 1-8 | Alu-Alu | 0.971 | 1.000 | 15,824 | 0.9575 | 0.9575 |
| 1-9 | Alu-L1 | 0.946 | 1.862 | 16,465 | 0.9579 | 0.9216 |
| 1-10 | Alu-LTR | 0.983 | 0.586 | 19,751 | 0.9598 | 0.9764 |
| 2-3 | LTR-Alu | 0.983 | 0.586 | 800 | 0.9536 | 0.9728 |
| 2-4 | LTR-L1 | 0.950 | 1.724 | 2,281 | 0.9538 | 0.9204 |
| 2-5 | LTR-L2 | 0.985 | 0.517 | 5,334 | 0.9543 | 0.9764 |
| 2-6 | LTR-Alu | 0.983 | 0.586 | 8,489 | 0.9548 | 0.9735 |
| 2-7 | LTR-SVA | 0.950 | 1.724 | 10,145 | 0.9550 | 0.9224 |
| 2-8 | LTR-Alu | 0.983 | 0.586 | 11,912 | 0.9556 | 0.9740 |
| 2-9 | LTR-L1 | 0.950 | 1.724 | 12,553 | 0.9558 | 0.9238 |
| 2-10 | LTR-LTR | 0.968 | 1.103 | 15,839 | 0.9575 | 0.9531 |
| 3-4 | Alu-L1 | 0.946 | 1.862 | 1,200 | 0.9537 | 0.9138 |
| 3-5 | Alu-L2 | 0.994 | 0.207 | 4,253 | 0.9541 | 0.9905 |
| 3-6 | Alu-Alu | 0.971 | 1.000 | 7,408 | 0.9546 | 0.9546 |
| 3-7 | Alu-SVA | 0.917 | 2.862 | 9,064 | 0.9549 | 0.8709 |
| 3-8 | Alu-Alu | 0.971 | 1.000 | 10,831 | 0.9552 | 0.9552 |
| 3-9 | Alu-L1 | 0.946 | 1.862 | 11,472 | 0.9554 | 0.9170 |
| 3-10 | Alu-LTR | 0.983 | 0.586 | 14,758 | 0.9569 | 0.9747 |
| 4-5 | L1-L2 | 0.986 | 0.483 | 1,600 | 0.9537 | 0.9776 |
| 4-6 | L1-Alu | 0.946 | 1.862 | 4,755 | 0.9542 | 0.9147 |
| 4-7 | L1-SVA | 0.878 | 4.207 | 6,411 | 0.9545 | 0.8086 |
| 4-8 | L1-Alu | 0.946 | 1.862 | 8,178 | 0.9547 | 0.9157 |
| 4-9 | L1-L1 | 0.931 | 2.379 | 8,819 | 0.9548 | 0.8925 |
| 4-10 | L1-LTR | 0.950 | 1.724 | 12,105 | 0.9556 | 0.9235 |
| 5-6 | L2-Alu | 0.994 | 0.207 | 2,500 | 0.9539 | 0.9905 |
| 5-7 | L2-SVA | 0.993 | 0.241 | 4,156 | 0.9541 | 0.9889 |
| 5-8 | L2-Alu | 0.994 | 0.207 | 5,923 | 0.9544 | 0.9906 |
| 5-9 | L2-L1 | 0.986 | 0.486 | 6,564 | 0.9545 | 0.9779 |
| 5-10 | L2-LTR | 0.985 | 0.517 | 9,850 | 0.9550 | 0.9767 |
| 6-7 | Alu-SVA | 0.917 | 2.862 | 1,400 | 0.9537 | 0.8675 |
| 6-8 | Alu-Alu | 0.971 | 1.000 | 3,167 | 0.9540 | 0.9540 |
| 6-9 | Alu-L1 | 0.946 | 1.862 | 3,808 | 0.9541 | 0.9145 |
| 6-10 | Alu-LTR | 0.983 | 0.586 | 7,094 | 0.9546 | 0.9734 |
| 7-8 | SVA-Alu | 0.917 | 2.862 | 200 | 0.9535 | 0.8669 |
| 7-9 | SVA-L1 | 0.878 | 4.207 | 841 | 0.9536 | 0.8048 |
| 7-10 | SVA-LTR | 0.950 | 1.724 | 4,127 | 0.9541 | 0.9209 |
| 8-9 | Alu-L1 | 0.946 | 1.862 | 400 | 0.9536 | 0.9136 |
| 8-10 | Alu-LTR | 0.983 | 0.586 | 3,686 | 0.9541 | 0.9731 |
| 9-10 | L1-LTR | 0.950 | 1.724 | 2,800 | 0.9539 | 0.9205 |

Table 2 Footnotes
[1] I:D values for repetitive element pairs for PSNs (Pair Sequence Numbers) 11-50 are taken from FIG. 4.

[2] The interaction between two inverted repetitive elements is directly proportional to their respective departures of their genome-wide I:D ratios from unity (1.0). Consequently, a proper comparison between the I:D ratios of a given repetitive element pair to the I:D ratio of Alu-Alu pairs should be made by comparing their respective departures from unity. This "departure from unity factor" is defined as $$(1.0 - I:D \text{ of all repetitive element pairs}) + (1.0 - I:D \text{ of all Alu-Alu pairs})$$

It should be noted that these I:D values are for the PSNs taken from FIG. 6.
[3] Spacer sizes are taken from FIG. 7 and include the lengths of each repetitive element that are also provided in this figure.
[4] This column provides the estimate of the I:D ratio for each repetitive pair identified in FIG. 7. It is obtained by adjusting the Alu-Alu pair I:D ratio obtained in column 6, $\tau\delta$, by the multiplier, $\mu$, determined from column 4.

Example 2

A Simplified Estimate of the Composite Stability of the L2 Element Examined in Example 1

This patent application claims that two homologous, inverted repetitive elements can interact when separated by 500,000 base pairs or less. Within this spacer size limit, an inverted pair interaction can occur with any other homologous element that is located either 5' or 3' (upstream or downstream) of an element. The final estimated stability of a given repetitive element is derived from the product of the square root of all the estimated I:D ratios for each inverted pair that is formed. The estimated stability of a repetitive element is therefore described by the following equation. This equation is adapted from patent application Ser. No. 14/154,303.

$$\text{Estimated Stability of a Repetitive Element} = \prod_{\text{Spacer Size}=-500,000\ bp(5')}^{\text{Spacer Size}=500,000\ bp(3')} \sqrt{I:D \text{ of Inverted Pairs}}$$

Repetitive element landscapes, as defined in this patent application, typically contain tens of thousands of repetitive elements. For example, the BRCA1 repetitive element landscape as described in FIG. 6 contains 44,408 repetitive elements. To simplify the math, this example estimates the stability of the L2 element which resides within the ten repetitive elements that are located in the landscape represented in FIG. 7. Note that this L2 element is identified as repetitive element number 5 in this figure. Table 3 identifies the six possible inverted pair interactions that may occur with this L2 element and calculates the individual stabilities from the I:D values estimated in Table 2.

TABLE 3

Repetitive DNA Element Pair I:D Estimates from FIG. 7

| Repetitive Element Pairs (Numbers) | Repetitive Element Pair (Types) | Is the Pair in FIG. 7 Inverted? (Yes or No) | Estimated I:D for Repetitive Element Pairs (Column 7, Table 1) | Estimated Partial Stability of L2 Element from Interaction with Other Member of Repetitive Pair ($\sqrt{I:D of InvertedPair}$) |
|---|---|---|---|---|
| 1-5 | Alu-L2 | No | 0.9907 | Direct Pair |
| 2-5 | LTR-L2 | Yes | 0.9764 | 0.9881 |
| 3-5 | Alu-L2 | Yes | 0.9905 | 0.9952 |
| 4-5 | L1-L2 | Yes | 0.9776 | 0.9887 |
| 5-6 | L2-Alu | No | 0.9905 | Direct Pair |
| 5-7 | L2-SVA | Yes | 0.9889 | 0.9944 |
| 5-8 | L2-Alu | Yes | 0.9906 | 0.9953 |
| 5-9 | L2-L1 | Yes | 0.9779 | 0.9889 |
| 5-10 | L2-LTR | No | 0.9767 | Direct Pair |

Using the simplified repetitive element landscape illustrated in FIG. 7, the estimated stability of the L2 Element in this figure is calculated as follows:

Estimated stability of $L2$ element=0.9881×0.9952× 0.9887×0.9944×0.9953×0.9889=0.9516

Examples 1 and 2 reflect Example 1 of patent application Ser. No. 14/154,303.

What I claim in my invention is:

1. A method for detecting the presence of cancer in a sample, comprising:
   A) obtaining a reference sample from an individual, and a clinical sample from an individual;
   B) determining a genome sequence data of the reference sample;
   C) Identifying regions of genomic instability in the genome sequence data of the reference sample, comprising at least Alu, SVA, LINE element data, Doomsday-junction data, deletion size frequency distribution, and cancer-linked region data;
   D) constructing multiplex primers to amplify regions of genomic instability as defined in step C;
   E) Performing amplification on the clinical sample using the primers of step D, to amplify regions of genomic instability;
   F) sequencing the amplified material of step E to provide clinical sample genome sequence data;
   G) identifying clustering of LINE, SVA and Alu elements within the reference genome sequence data and clustering of repetitive elements within the clinical genome sequence data, wherein
      I. a cluster of Alu elements within the reference genome can be interspersed with one or more LINE elements and/or SVA elements; and wherein
      II. the adjacent elements within Alu element clusters within the reference genome are separated by up to 100 base pairs; and wherein
      III. a cluster of repetitive elements within the clinical genome are separated by up to 100 base pairs; and wherein
      IV. inverted Alu pairs within the reference genome and repetitive elements within the clinical genome interact to form a Doomsday junction, a double-strand break generating DNA structure;
   H) categorizing Alu pairs in the reference genome and repetitive elements within the clinical genome according to the four possible clustering configurations;
      I. both Alus in the pair within the reference genome and both repetitive elements within the pair in the clinical genome reside within the same cluster,
      II. both Alus in the pair within the reference genome and both repetitive elements within the pair in the clinical genome reside in different clusters,
      III. only one Alu within the pair within the reference genome and both repetitive elements within the pair in the clinical genome resides within a cluster, or
      iv. neither Alu in the pair within the reference genome and both repetitive elements within the pair in the clinical genome resides within a cluster;
   I) further categorizing the Alu pairs in the reference genome by the number of base pairs within the spacer separating the two Alu elements which form the Alu pair and further categorizing the repetitive element pairs in the clinical genome by the number of base pairs within the spacer separating the two repetitive elements which form the repetitive element pair;
   J) further categorizing the Alu pairs in the reference genome by the number of Alus within the spacer separating the two Alus which form the Alu pair and further categorizing the repetitive element pairs in the clinical genome by the number of repetitive elements within the spacer separating the two repetitive elements which form the repetitive element pair;
   K) calculating the imbalances between inverted and direct oriented Alu element pairs within the entire reference genome according to steps H), I) and J); assigning the appropriate imbalance to each inverted repetitive element pair within the genome that reside within three million base pairs of a cancer-linked region according to step G);
      I. wherein the frequency of inverted and direct Alu element pairs within the reference genome is expressed in a Alu pair I:D ratio according to H), I), and J) and wherein the frequency of inverted and direct repetitive element pairs within the clinical genome is expressed in a repetitive element pair I:D ratio according to H), I), and J);

II. wherein the assigned Alu pair I:D ratio is the estimated stability of a single inverted repetitive element pair within the clinical genome;

III. wherein a single repetitive element has a specific likelihood of forming a double-strand break from interacting with each of its 110 adjacent inverted repetitive element pair neighbors in the 5' direction and from interacting with each of its 110 adjacent inverted repetitive element pair neighbors in the 3' direction according to step G); and wherein the likelihood of each double-strand break is used to calculate the total instability of the end of each repetitive element;

iv. wherein the stability of each end of each repetitive element for a single inverted repetitive element pair interaction in the clinical genome is the fourth root of the assigned Alu pair I:D ratio according to step K)-ii; and v. wherein the composite stability of each end of each repetitive element within three million base pairs of a cancer-linked region is calculated by multiplying all individual inverted repetitive element end stabilities as described in step K)-iv;

L) calculating the distance in base pairs between the end of each repetitive element within three million base pairs of a cancer-linked region of the clinical genome according to step K);

M) constructing a deletion size probability distribution which describes the probability that a deletion of a given size or larger that will not result from a double-strand break according to step K) using a human genome deletion size frequency distribution;

N) determining the individual stability of the cancer-linked region as related to a single end of a repetitive element by multiplying the composite stability of each end of a repetitive element according to step K)-vi by the likelihood that the double strand break will not create a deletion large enough to extend into the cancer-linked region of the genome according to step M);

O) determining the composite stability of the cancer-linked region by multiplying the products of each individual stability for each respective end of a repetitive element within three million base pairs of the cancer-linked region according to step N);

P) determining an individual's susceptibility to cancer by comparing the composite stability of a cancer-linked region according to step O) for the clinical genome to the composite stabilities calculated for that same cancer-linked region for a group of individuals that have developed cancer as a result of genome damage to that same region of the genome; and wherein the lower the stability, the greater the susceptibility to cancer;

Q) detecting the presence of damaged DNA within the cancer-linked region of the clinical genome sequence data by sequencing the amplified sample of step E) at the cancer-linked regions identified in step P); wherein the presence of damaged DNA within the cancer-linked regions identified in step P in the clinical sample is indicative of the presence of cancer.

* * * * *